(12) United States Patent
Salafia et al.

(10) Patent No.: US 10,572,808 B2
(45) Date of Patent: Feb. 25, 2020

(54) SYSTEM AND METHOD FOR PREDICTING FETAL AND MATERNAL HEALTH RISKS

(71) Applicant: MONTCLAIR STATE UNIVERSITY, Montclair, NJ (US)

(72) Inventors: Carolyn M. Salafia, Larchmont, NY (US); Diana M. Thomas, Randolph, NJ (US)

(73) Assignee: Montclair State University, Montclair, NJ (US)

( * ) Notice: Subject to any disclaimer, the term of this patent is extended or adjusted under 35 U.S.C. 154(b) by 747 days.

(21) Appl. No.: 15/126,652

(22) PCT Filed: Mar. 30, 2015

(86) PCT No.: PCT/US2015/023257
§ 371 (c)(1),
(2) Date: Sep. 16, 2016

(87) PCT Pub. No.: WO2015/153409
PCT Pub. Date: Oct. 8, 2015

(65) Prior Publication Data
US 2017/0091402 A1  Mar. 30, 2017

Related U.S. Application Data

(60) Provisional application No. 61/973,565, filed on Apr. 1, 2014.

(51) Int. Cl.
*G06N 5/04* (2006.01)

(52) U.S. Cl.
CPC ..................................... *G06N 5/04* (2013.01)

(58) Field of Classification Search
CPC ....................................................... G06N 5/04
See application file for complete search history.

(56) References Cited

U.S. PATENT DOCUMENTS

| 6,024,701 A * | 2/2000 | Almog | G16H 50/50 600/300 |
|---|---|---|---|
| 2003/0135130 A1* | 7/2003 | Hoctor | A61B 5/0488 600/546 |
| 2011/0081059 A1* | 4/2011 | Salafia | G06T 7/0012 382/128 |

* cited by examiner

Primary Examiner — Vincent Gonzales
Assistant Examiner — Seth Andrew Raker

(57) ABSTRACT

Provided herein is a method, a programmed computer and an article of manufacture for predicting a prenatal, neonatal, obstetric or childhood clinical event, disease or disorder, as well as a method for generating in-utero fetal and placental growth curves, using a continuous recursive algorithm housed in a computer and data periodically collected during pregnancy.

16 Claims, 13 Drawing Sheets

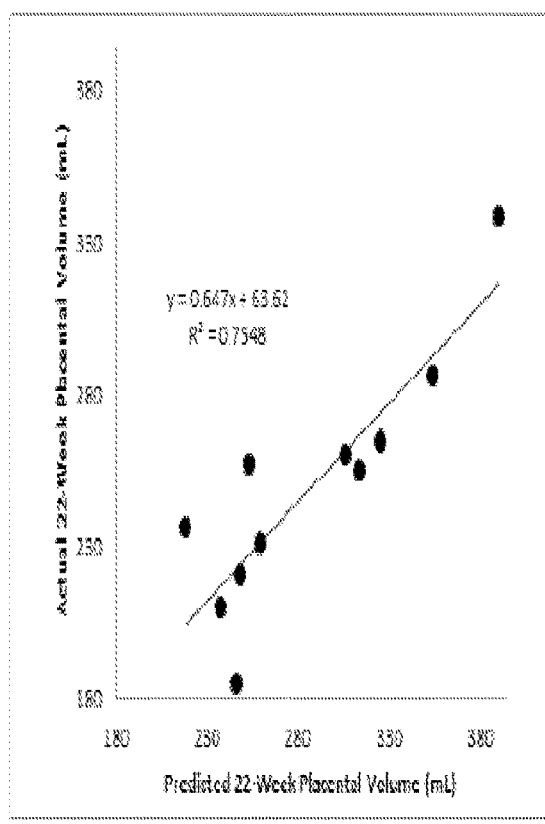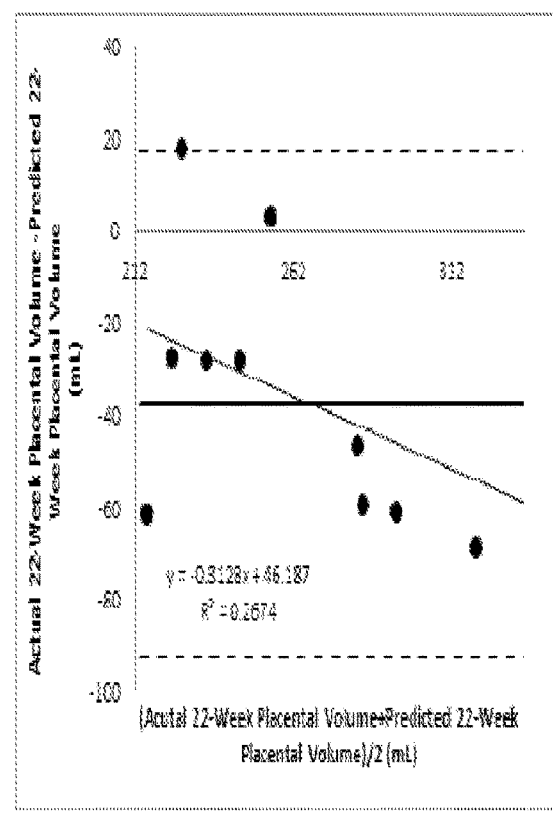
FIG. 3A  FIG. 3A'

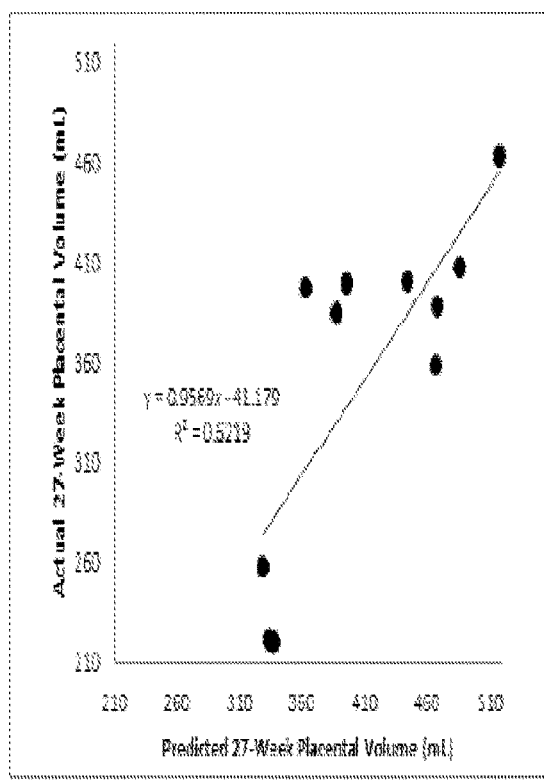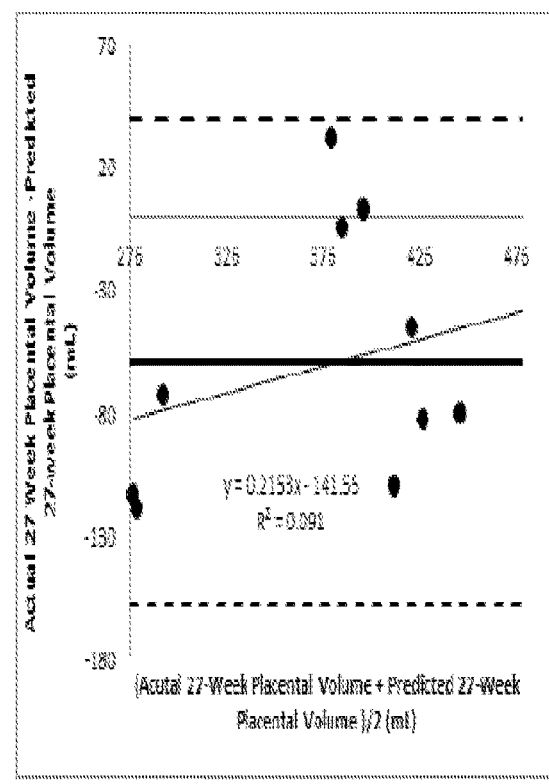
FIG. 3B  FIG. 3B'

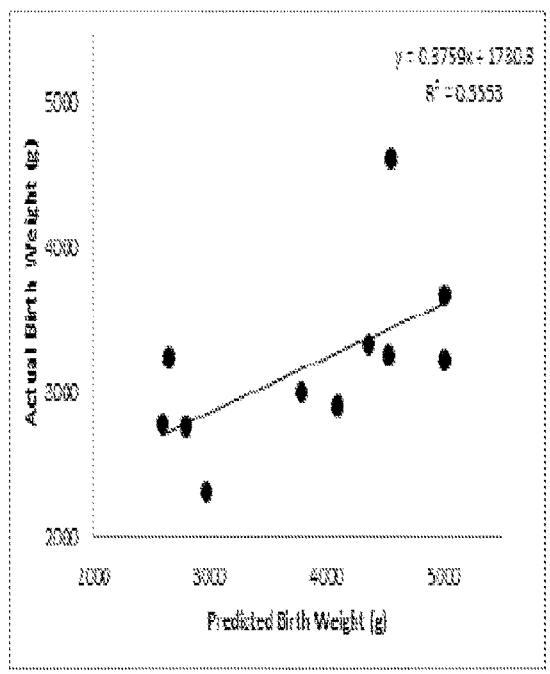
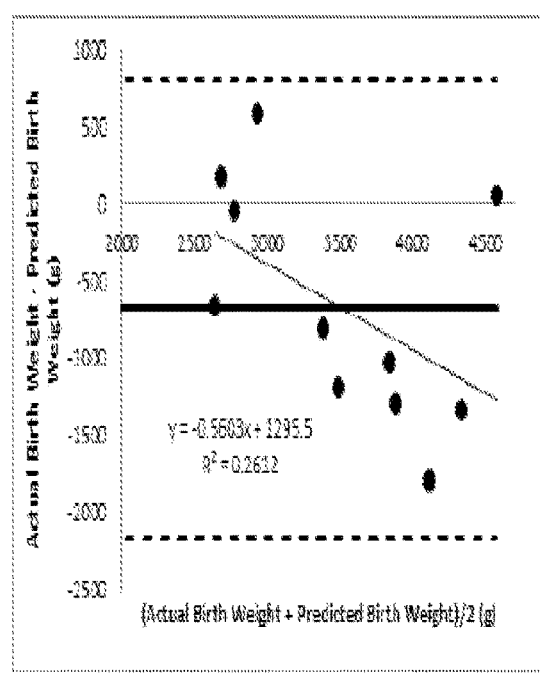
FIG. 3C
FIG. 3C'

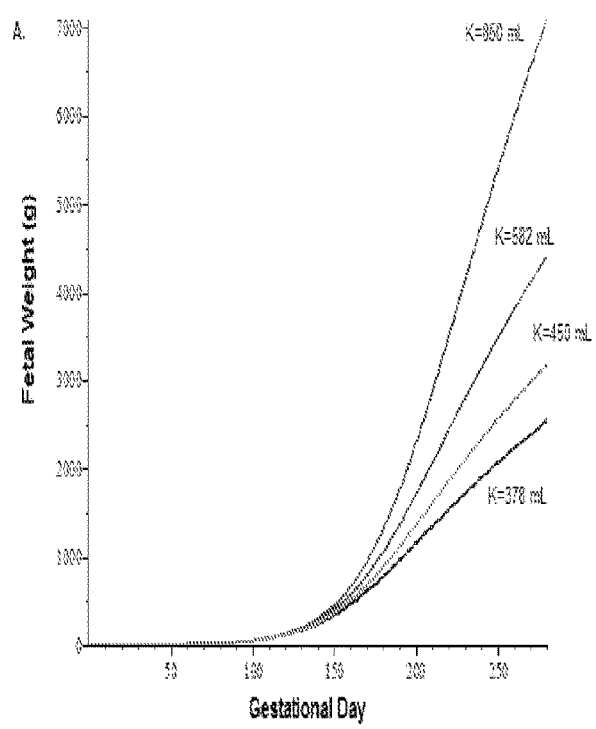
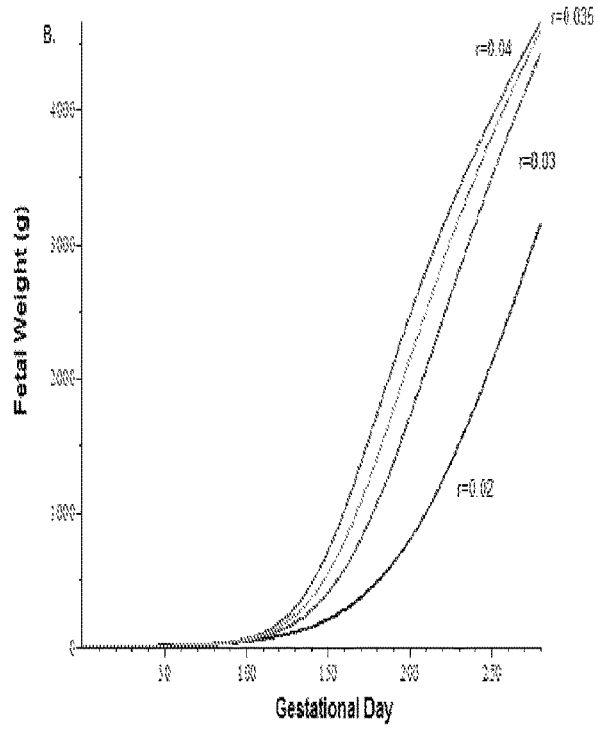
FIG. 4A                    FIG. 4B

| List of proposed measurements, descriptions, and known relations to pregnancy complications. | | | |
|---|---|---|---|
| Measurement | Calculation | Explanation | Pregnancy Complications |
| Mean Cord Distance | Average of distances from cord insertion site to placental perimeter. | Describes lateral placental growth. | A proxy for placental radius used in combination with other metrics. |
| Minimal Cord Distance | Minimum of distances from cord insertion site to placental perimeter. | Smaller values imply higher marginal cord insertion. | First trimester marginal cord insertion influences thickness. |
| Mean Placental Diameter | Average of diameters across the cord insertion site to the placental perimeter | Describes lateral placental growth. | A measure related to placental area and normalize other metrics. |
| Placental Area | $\pi r^2$ where $r$ =mean placental diameter/2 | Proxy for chorionic plate area. | A simple metric used in combination with other metrics. |
| Placental Volume (PV) | Volume determined by 3D ultrasound. | Proxy for placental weight. | Reduced PV related to SGA birth weight and preeclampsia. |
| Placental Quotient | Placental Volume/Fetal Crown Rump Length | Adjustment for placental volume by gestational age. | Lower quotient linked to SGA, preeclampsia, pre-term birth. |
| Placental Morphology Index (PMI) | Mean Placental Diameter/Placental Quotient | Measures placental thickness. Higher PMI related to longer and flatter placenta. | High PMI SGA, preeclampsia, spontaneous pre-term birth before 37 weeks. |
| Geometrical Center | With the cord insertion site as the origin, the average of the points on the perimeter of the placenta | Quantifies the "center" of the placenta | Non-central cord insertion site linked to sparser chorionic vascular tree. |
| Mean Cord Insertion Distance | Distance from cord insertion site to geometric center | The smaller the distance, the more central the cord insertion site. | Non-central cord insertion site linked to sparser chorionic vascular tree. |
| Cord Centricity | Minimal sampled placental diameters/maximal sampled placental diameters | The closer the cord centricity is to 1, the more central the cord insertion site. | Non-central cord insertion site linked to sparser chorionic vascular tree. |
| Cord Eccentricity | Standard deviation of sampled placental radii × 100/average of the sampled placental radii | The larger the cord eccentricity, the more eccentric cord insertion site. | Non-central cord insertion site linked to sparser chorionic vascular tree. |
| Deviation from roundness | mean square deviation of segmented placental radii from geometrical center | The smaller the deviation, the more regular the placental shape. | Irregular shapes imply sparser chorionic surface vascularization and smaller birth weight. |
| Variable disk thickness | Standard deviation of mean placental diameter / placental quotient | A large standard deviation indicates higher variation in disk thickness. | Related to deformed placental vascular growth, decreased placental efficiency, and a smaller baby for a given placental weight. |
| Mean chorionic vascular distance | Average of a chorionic surface pixel to the nearest chorionic vessel/placental diameter | Measures denseness of vascular tree. Large MCVD imply sparse vascular trees. | Large MCVD linked to reduced placental efficiency and smaller baby for placental weight. |
| Mean placental diameter ratio | Ratio of the smallest sampled placental diameters to the largest sampled placental diameters | MPDR closer to 1 relates to a more regular shaped placenta. | Irregular shapes linked to sparser vascular tree and reduced placental efficiency. |
| Placental Irregularity Index | Standard Deviation of the sampled placental diameters × 100/MPD | Smaller index linked to more regular placental shape | Irregular shapes linked to sparser vascular tree. |
| $\alpha$ | $\alpha$=(Placental Weight)/(Fetal Weight)$^{3/4}$ | Lower $\alpha$ implies placental less efficient in transferring nutrients to the fetus. | Lower $\alpha$ associated with SGA birth weight. |
| $\beta$ | $\ln$(Placental Weight)/$\ln$(Fetal Weight) | Measures efficiency placental capacity to nourish fetus. | Higher $\beta$ associated with SGA birth weight. |

Fig. 7

| Baseline characteristics and available measurements in pooled database. Tri.1,2=trimester 1 and 2, Fetal=Fetal measurements, Term = Placental measures at term, MA= maternal age at baseline, BMI= maternal body mass index at baseline. [1]Database sub-cohort of trimester 2 measures. [2]Infant measures at term. [3]Data includes 31 GDM pregnancies. [4]Data exclusively contains pre-term births with pregnancy complications and placental morphology measures. | | | | | | | |
|---|---|---|---|---|---|---|---|
| Location (N) | GWG | Tri. 1 | Tri. 2 | Term | Fetal | MA | BMI |
| [1]WUSL (750) | X | X | X | | X | 31.6±5.6 | 28.4±7.5 |
| [2]PIN (967) | X | | | X | | 27.7±6.2 | 25.0±6.6 |
| [1]NYU (135) | | X | X | X | X | 33.9±4.2 | 23.2±3.6 |
| [3]CWRU (83) | X | X | | | | 26.9±1.2 | Lean 22.0±1.9 / Obese 38.4±6.3 |
| UPenn (600) | X | X | X | | X | 30.7±5.8 | 27±6.9 |
| [4]UConn (465) | | | | X | X | 27.6±6.6 | ----- |
| [5]PBRC (80) | X | X | X | X | X | ----- | ----- |

FIG. 8

| Correlation between β and additional pregnancy complications. | |
|---|---|
| Marker | r |
| High Diastolic Blood Pressure | -0.26 |
| High Systolic Blood Pressure | -0.20 |
| Increased Presence of Placental Knots | -0.17 |
| Fibrotic Chorionic Villi | -0.17 |
| Intrauterine Growth Restrict. | -0.15 |
| Intraventicular Hemorrhage | 0.18 |
| Placental Edema | 0.19 |
| Fetal Acute Inflammation | 0.20 |
| Chorioamnionitis | 0.21 |
| Maternal diastolic blood presssure | 0.22 |
| Amnion necrosis | 0.23 |
| Acute Inflammation | 0.23 |
| Any maternal acute inflammation | 0.23 |
| Acute amnionitis | 0.26 |

FIG. 9

| Study Name/Study Description | Study Location | Maternal Age (years) | Gestational Age at Delivery (days) | Gravidity | Data Application |
|---|---|---|---|---|---|
| Multi-point (N=11) Five longitudinal ultrasound measures of placental volume. | Livingston, NJ | 31.5 ±2.9 | 272.6±13.5 | 1.8 ±1.2 | Estimate gestational age at inflection point. Calculate the values of $r$ and $K$. Validate model predictions of placental volume. Validate model predictions of birth weight. |
| Early pregnancy (N=54) One measure of placental volume during early pregnancy and one measure of placental weight at term with a record of known pregnancy complications. | Philadelphia, PA | 33.2±4.5 | 274.5±8.5 | | Calculate the values of $r$ and $K$. Locate pregnancy complications within quartiles of $r$ and $K$. |

FIG. 10

|  | P0 | r | K | Gestational Age at Inflection Point |
|---|---|---|---|---|
| Multi-point study (all N=11) | 59.085±15.258 | 0.035±0.008 | 581.702±157.256 | 22.212±3.388 |
| Early pregnancy study (all N=54) | 73.139±19.946 | 0.031±0.006 | 473.861±94.585 | ---------- |
| Early Pregnancy study (uncomplicated pregnancies N=43) | 71.218±20.907 | 0.031±0.006 | 475.412±101.079 | ---------- |
| Early pregnancy study (pregnancies with complications N=11) | 80.476±14.211 | 0.028±0.005 | 467.940±67.695 | ---------- |

FIG. 11

SYSTEM AND METHOD FOR PREDICTING FETAL AND MATERNAL HEALTH RISKS

PRIORITY TO RELATED APPLICATIONS

This application is a National Stage Application of PCT/US2015/023257 filed Mar. 30, 2015, which claims the benefit of priority to U.S. 61/973,565, filed on Apr. 1, 2014. Each of prior mentioned applications is hereby expressly incorporated herein by reference.

FIELD OF THE INVENTION

The invention relates to a continuous recursive algorithm housed in a computer for predicting fetal, childhood and maternal health risks.

All publications, patents, patent applications, and other references cited in this application are incorporated herein by reference in their entirety for all purposes and to the same extent as if each individual publication, patent, patent application or other reference was specifically and individually indicated to be incorporated by reference in its entirety for all purposes. Citation of a reference herein shall not be construed as an admission that such is prior art to the present invention.

BACKGROUND OF THE INVENTION

Advances in both ultrasound technology and quantitative analysis of the placenta have permitted detailed assessment of key prenatal placental landmarks such as centrality of the cord insertion site, chorionic surface vascularization, the fetal-placental scaling exponent 3 (measure of placental vascular fractal structure); placental thickness and its variability, and placental roundness. Abnormal placental growth has been linked to adverse pregnancy outcomes including preeclampsia, intrauterine growth restriction, preterm labor, and stillbirth. There is increasing evidence linking abnormal placental and fetal development, referred to as fetal programming, to long-term health consequences in the offspring, extending even into adulthood. Indeed, birth weight has already been linked to later cardiovascular health and type 2 diabetes. It is believed that fetal programming is a result of inefficient fetal-placental nutrient exchange but the exact mechanism is not well understood. Often aspects of these important placental growth patterns can be identified by ultrasonographic examination at the end of the first trimester.

The ability to identify at risk placental growth patterns early in pregnancy, e.g., before the pregnancy is clinically compromised, would significantly impact both obstetric care and also initiate preventative measures even before birth. And despite growing evidence that deviations from normal placental morphology and growth trajectory early in pregnancy mark risk for adverse pregnancy outcomes for both the child and mother, an accessible and user-friendly, evidence-based algorithm to predict risk does not exist. Thus, there is a need for a recursive placental growth model to predict fetal, childhood and maternal health risks.

SUMMARY OF THE INVENTION

The present invention is directed to a method for predicting a prenatal, neonatal, obstetric or childhood clinical event, disease or disorder from data collected during a pregnancy, comprising the steps of:

inputting periodically collected pregnancy data comprising placental and obstetric data into a database housed in a computer;

applying a continuous recursion modeling algorithm to said inputted pregnancy data to generate fetal and placental growth data during said pregnancy;

generating data showing any deviations from model predictions of normal fetal and placental growth when compared to said generated fetal and placental growth data during said pregnancy; and predicting a prenatal, neonatal, obstetric or childhood risk of an adverse clinical event, disease or disorder from said deviating data.

The invention is further directed to a method for generating in-utero fetal and placental growth curves from data collected during a pregnancy, comprising the steps of:

inputting placental and obstetric data collected from said pregnancy into a database housed in a computer; and applying a continuous recursion modeling algorithm to said pregnancy data to generate said in-utero fetal and placental growth curves during said pregnancy.

The invention is also directed to a computer programmed to predict a prenatal, neonatal, obstetric or childhood clinical event, disease or disorder from data collected during a pregnancy, comprising software which:

applies a continuous recursion modeling algorithm to data collected during said pregnancy, and inputted into said computer, to generate in-utero fetal and placental growth data; and outputs data showing any deviations of said in-utero fetal and placental growth data from model predictions of normal in-utero fetal and placental growth.

The invention still further is directed to an article of manufacture for predicting a prenatal, neonatal, obstetric or childhood clinical event, disease or disorder from data periodically collected during a pregnancy, comprising a non-transitory computer-readable storage medium, and code stored on the medium, the code, when executed on a processor, controlling the processor for measuring in-utero fetal and placental growth during said pregnancy, wherein the processor applies a continuous recursion modeling algorithm to said data periodically collected during said pregnancy to show any deviations of said data periodically collected during said pregnancy from model values of normal placental volume to predict said prenatal, neonatal, obstetric or childhood clinical event, disease or disorder.

BRIEF DESCRIPTION OF THE DRAWINGS

The drawings described below are for illustrative purposes only and are not intended to limit the scope of the invention.

FIG. 3 shows placental weight and volume validation.

FIG. 4 shows value of r influenced early fetal growth while the value of impacted later fetal growth.

FIG. 7 is a table showing that placental quantifiers can be measured in the first trimester of pregnancy and are related to placental evaluations at term.

FIG. 8 is a table showing baseline characteristics and available measurements in a pooled database.

FIG. 9 is a table showing correlation between and additional pregnancy complications.

FIG. 10 is a table showing the physical and other characteristics of the women who completed the study of Example 1.

FIG. 11 is a table showing the breakdown of parameter estimates (X±SD) by study, pregnancies without complications, pregnancies with complications, and total pregnancies.

DETAILED DESCRIPTION

Figure 6:
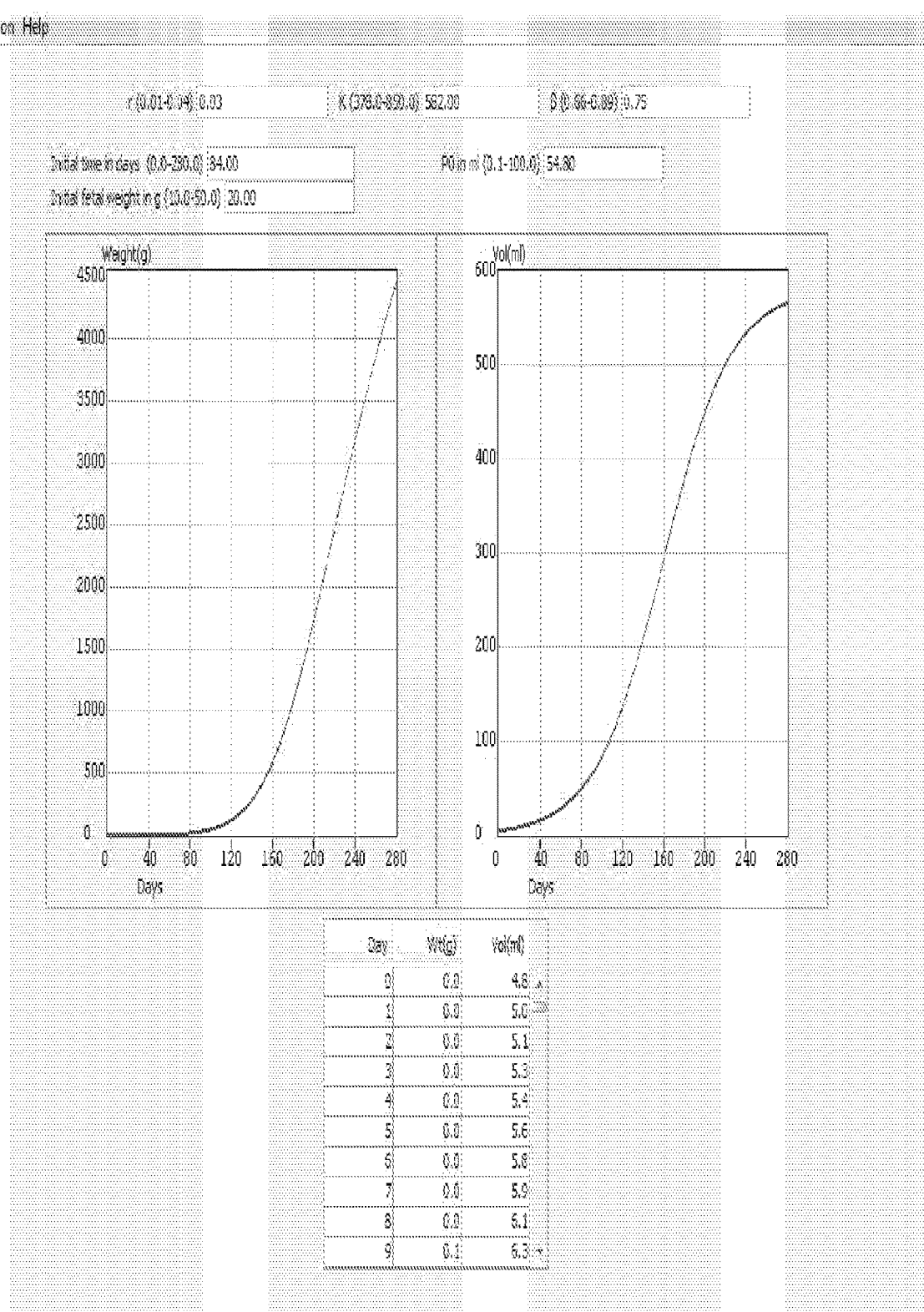
FIG. 6 is a screen shot of the placental-growth curve software used in an embodiment of the invention.

The invention is based in part on the discovery that by applying recursive algorithmic models from placental measures collected at multiple times during gestation, dynamic changes in placental growth can be calculated, and normal versus at risk deviations in time dependent growth can be identified. The flexibility of recursion models allows broad model utility prospectively and retrospectively. Forward model simulations validate the use of placental morphology measures to predict adverse pregnancy outcomes. Reverse simulations can identify combinations of timing, number, and magnitude of gestational stressors that contributed to clinically unanticipated adverse outcomes. Identifying the placental origins of clinically unpredicted pregnancy complications permits optimal inter-pregnancy evaluation, counseling, and future pregnancy management. Models can be programmed into user-friendly computer interfaces. For example, FIG. 6 shows a screenshot of the computer output in an embodiment of the invention. Such models can be used, for example, in Phase 2 clinical work.

Thus, in one embodiment of the invention, provided is a method for predicting a prenatal, neonatal, obstetric or childhood clinical event, disease or disorder from data collected during a pregnancy, comprising the steps of:
  inputting periodically collected pregnancy data comprising placental and obstetric data into a database housed in a computer;
  applying a continuous recursion modeling algorithm to said inputted pregnancy data to generate fetal and placental growth data during said pregnancy;
  generating data showing any deviations from model predictions of normal fetal and placental growth when compared to said generated fetal and placental growth data during said pregnancy; and
  predicting a prenatal, neonatal, obstetric or childhood risk of an adverse clinical event, disease or disorder from said deviating data.

In another embodiment of the invention, provided is a method for predicting a prenatal, neonatal, obstetric or childhood clinical event, disease or disorder from data collected during a pregnancy, further comprising the step of performing a clinical intervention if said deviating data so warrants.

In another embodiment of the invention, provided is a method for predicting a prenatal, neonatal, obstetric or childhood clinical event, disease or disorder from data collected during a pregnancy, wherein a continuous recursion modeling algorithm is housed in a computer.

In another embodiment of the present invention, provided is a method for predicting a prenatal, neonatal, obstetric or childhood clinical event, disease or disorder from data collected during a pregnancy, wherein said prenatal, neonatal, obstetric or childhood clinical event, disease or disorder is preeclampsia, intrauterine growth restriction, preterm labor, stillbirth, type 2 diabetes, high diastolic blood pressure, high systolic blood pressure, increased presence of placental knots, fibrotic chorionic villi, intrauterine growth restrict, intraventicular hemorrhage, placental edema, fetal acute inflammation, chorioamnionitis, amnion necrosis, acute fetal inflammation, acute maternal inflammation or acute amnionitis.

In a further embodiment of the present invention, provided is a method for generating in-utero fetal and placental growth curves from data collected during a pregnancy, comprising the steps of:
  inputting placental and obstetric data collected from said pregnancy into a database housed in a computer; and
  applying a continuous recursion modeling algorithm to said pregnancy data to generate said in-utero fetal and placental growth curves during said pregnancy.

In a still further embodiment of the invention, provided is a computer programmed to predict a prenatal, neonatal, obstetric or childhood clinical event, disease or disorder from data collected during a pregnancy, comprising software which:
  applies a continuous recursion modeling algorithm to data collected during said pregnancy, and inputted into said computer, to generate in-utero fetal and placental growth data; and
  outputs data showing any deviations of said in-utero fetal and placental growth data from model predictions of normal in-utero fetal and placental growth.

In another embodiment of the present invention, provided is a computer wherein software further predicts a prenatal, neonatal, obstetric or childhood risk of an adverse clinical event, disease or disorder from said outputted data showing deviations.

In another embodiment of the present invention, provided is an article of manufacture for predicting a prenatal, neonatal, obstetric or childhood clinical event, disease or disorder from data periodically collected during a pregnancy, comprising:
  a non-transitory computer-readable storage medium, and code stored on the medium, the code, when executed on a processor, controlling the processor for measuring in-utero fetal and placental growth during said pregnancy, wherein the processor applies a continuous recursion modeling algorithm to said data periodically collected during said pregnancy to show any deviations of said data periodically collected during said pregnancy from model values of normal placental volume to predict said prenatal, neonatal, obstetric or childhood clinical event, disease or disorder.

Placental growth in volume and mass has been well-established to follow a sigmoidal pattern (FIG. 2), with early exponential growth followed by an inflection point and finally more limited log-like growth. Sigmoidal curves are common biological phenomena, from population dynamics, to plant growth, and cancer cell dynamics. Different classes of mathematical models mechanistically describe sigmoidal growth, the most popular of which is the logistic growth model. The logistic model assumes that initial growth is exponential but is eventually limited by a bound referred to as a carrying capacity. The carrying capacity for placental volume represents a theoretical cap on total possible volume capacity for which the placenta can hold, which may be higher than placental volume at term. Indeed, placental size continued to grow in late-term pregnancies providing observed evidence that the carrying capacity need not be attained during pregnancy.

The ability to identify at risk placental growth patterns early in pregnancy, before the pregnancy is obviously clinically compromised, will revolutionize obstetric care and has the potential to impact pediatric practice. Thus, the invention provides for the development and validation of evidence-based models to predict placental dysfunction and pregnancy complications from placental metrics obtained in early pregnancy. In one embodiment, the invention provides for a database containing information from over 2000 pregnancies and includes 3D ultrasound images of the placenta obtained at 11-14 weeks of gestation. From these images, 19 different placental morphology metrics can be calculated and analyzed together with data extracted from 2D digital placental images and placental histopathology samples collected at birth. The clinical histories of these pregnancies are available, including adverse outcomes such as premature membrane rupture, preeclampsia, pre-term labor, placental abruption, chronic inflammation, and gestational diabetes mellitus.

The associations of placental metrics from early gestation and delivery, and adverse pregnancy outcomes are used to construct pregnancy risk prediction models based on algorithms that identify individual placental metrics as outside of receiver operating characteristic (ROC) determined cut off values. The risk models validate the prospective, predictive value of novel measures of placental structure for adverse pregnancy outcomes.

In another embodiment, a second class of recursive models are developed from placental measures collected at multiple times during gestation to reflect the dynamic changes in placental growth, and identify normal versus at risk deviations in time dependent growth. The flexibility of recursion models allows broad model utility prospectively and retrospectively. As discussed above, forward model simulations validate the use of placental morphology measures to predict adverse pregnancy outcomes. Reverse simulations can identify combinations of timing, number, and magnitude of gestational stressors that contributed to clinically unanticipated adverse outcomes. Identifying the placental origins of clinically unpredicted pregnancy complications permits optimal inter-pregnancy evaluation, counseling, and future pregnancy management. Models will be programmed into user-friendly interfaces for Phase 2 clinical use.

In a further embodiment, the invention provides for an evidence-based algorithm for prediction of risk of placental dysfunction and adverse pregnancy outcomes that includes demographic and environmental covariates (maternal age, gestational age, height, body weight, race, parity, and trimester specific objectively determined energy intake) and placental morphology metrics obtained from 11-14 week 3D ultrasound data pooled from Washington University, St. Louis, New York University, and the University of Pennsylvania.

In a method of the invention, recursion modeling is applied to predict dynamics of placental growth. Using placental morphology measures obtained at multiple times during gestation, recursive formulations can model dependency of placental "state" during a given gestational week on the "state" of the placenta in the previous week(s) and account for the observed range of normal versus dysfunctional placental growth patterns. The inventive algorithms can be validated on a reserved test database containing first trimester placental measures and data regarding pregnancy outcomes. This step will produce objective criteria for the determination of "healthy" and "at risk" patterns of placental growth remote to delivery, and clinically unanticipated adverse outcomes. The inventive models yield individualized pregnancy risks, providing the basis for a personalized and proactive management plan for each pregnancy.

Placental quantifiers such as, for example, thickness, roundness, and cord insertion site can be measured in the first trimester of pregnancy and are related to placental evaluations at term. Measures of irregular placental shape obtained between 11-13 weeks (see FIG. 7) were negatively correlated with placental weight at term. The Placental Morphology Index (PMI) was negatively correlated with both the placental weight and chorionic plate area at term. First trimester metrics (cord insertion site, geometrical center, cord eccentricity) are correlated with the cord insertion site at term. Interestingly, the cord insertion site measures between 11-13 weeks of gestation are also related to thickness and mean chorionic vascular density suggesting non-central cord insertion site is a biomarker for a sparser chorionic vascular tree, inefficient placental-fetal nutrient exchange and a smaller baby at term.

Further, it was observed that non-central cord insertion site, non-round placental shape, and variable placental thickness are also related to a sparser chorionic vascular tree and lower placental efficiency. Cord displacement is positively correlated with mean thickness. On the other hand, deformation of the placental chorionic surface shape corresponds to lower but more variable placental disk thickness. A placenta with thin regions reflecting reduced villous arborization and variable fetal stem branching will tend to be less functionally efficient, and will yield a smaller baby for given placental weight.

Placental volume, placental quotient, placental morphology index, and mean cord diameter predicts small for gestational age (SGA), preeclampsia and spontaneous pre-term birth. A recent study conducted by the inventors evaluated placental volume, placental quotient, and the PMI in weeks 11-13 of pregnancy and related these measures to pregnancy outcomes at term. Placental volume served as a proxy for placental weight. The placental quotient adjusts placental volume for gestational age. Mean cord diameter represents lateral placental growth. PMI indicates placental thickness (higher PMI is related to a flatter placenta). Deviations of all four measures from normal values were significantly correlated to adverse pregnancy outcomes: SGA, preeclampsia, and spontaneous preterm birth.

The proportion of the placenta that is metabolically active ($\alpha$) and the fetal-placental scaling exponent ($\beta$) predicts preeclampsia, inflammation, placental abruption, and pre-term membrane rupture. The fetal-placental relationship is nonlinear and follows an allometric scaling law: $PW=\alpha FW^\beta$ (PW=placental weight and FW=fetal weight). In term pregnancies with normal outcomes, $\alpha=1$ and $\beta=0.75$. Across gestation, the value of $\alpha$ decreases to 1 and $\beta$ should remain close to 0.75 by the end of the second trimester. Deviations in $\alpha$ and $\beta$ are highly sensitive indicators of pregnancy complications. In fact, the inventors have noted that of over 400 pre-term births, $\alpha$ and $\beta$ are predictors of preeclampsia, chorionic inflammation, placental abruption, and pre-term membrane rupture.

Figure 1:
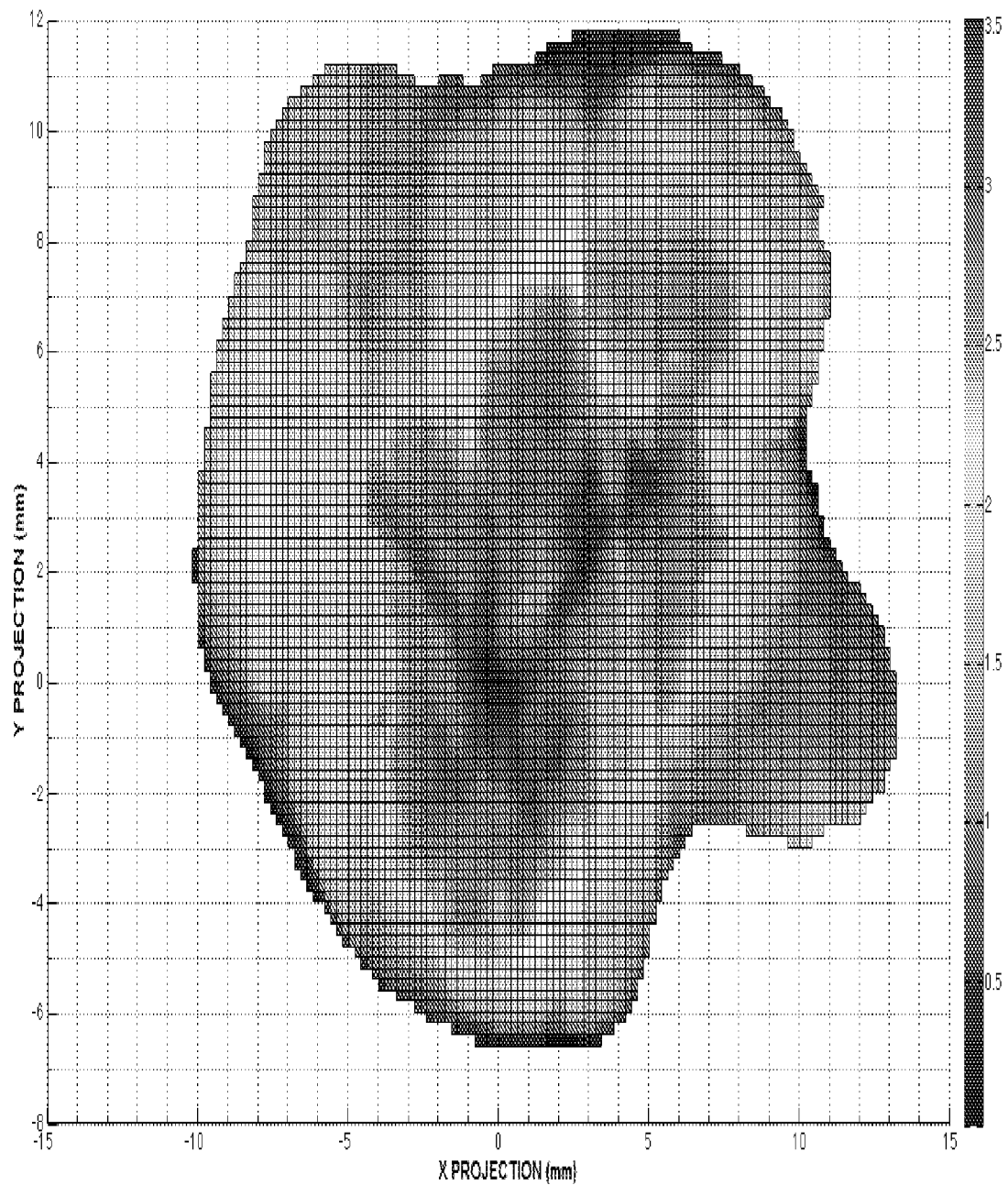
FIG. 1 shows a placental thickness map.

More specifically, placental growth is a recursive process which varies over time. A recursive dynamic model that predicts time-varying placental vascular tree formation was recently co-developed by one of the inventors. Model simulations suggested that deviations from normal placental morphology (round, regular, centrally inserted cord placement) early in pregnancy are amplified over the course of gestation. Cord displacement, placental disk diameter, chorionic plate area, perimeter, and maximal radius calculated from the cord insertion point were found to have power-law distributions, indicating that small early perturbations in morphology recursively are amplified in future placental growth, experimentally supporting conclusions derived from the recursion model. The initial recursion model can be further advanced using new topological visualizations of placental growth with graphic display of variation in arborization (FIG. 1). The topological visualization can be analyzed much as a geologist analyzes strata and provide novel opportunities for model development that will time onset of deviations from normal growth trajectory. The relationship of 3D villous arborization to the networks of distributing chorionic surface arteries and draining venous vasculature may be key to understanding variation in placental function (see also U.S. Pat. No. 8,565,507, which is incorporated herein by reference).

In a further embodiment, the invention provides for a synopsis of the fetal-maternal in-utero processes as early as 11 weeks. Using existing 3 D ultrasound recordings and at birth placenta and clinical pregnancy data, the invention provides for the first class of models that combine 19 different placental measures to identify and estimate risk for adverse pregnancy outcomes.

In a further embodiment of the invention, ultrasound and pregnancy data were pooled from approximately 2,335 pregnancies (FIG. 8). All placental measures were obtained from singleton pregnancies. At Washington University St. Louis (WUSL) 3D power Doppler placental images were obtained in women (n=750) between 11 and 14 weeks of pregnancy and again in the second trimester. Gestational weight gain and fetal biometric parameters were recorded. Placental measures in the Pregnancy, Infection and Nutrition (PIN) study conducted at the University of North Carolina (n=967), were obtained at delivery. Placentas were weighed to the nearest gram, photographed and histology samples obtained. New York University (NYU): Eighty of the women in this study (n=135) were recruited 11-14 weeks in gestation when they appeared for routine aneuploidy screening. At delivery, placenta were weighed to the nearest gram, photographed and histology samples obtained. (98 have 11-14 week and delivery measures). At Case Western Reserve University (CWRU), (n=83) women were recruited at the time of elective cesarean delivery at term. Placenta weight to the nearest gram was recorded by the water displacement method. In an on-going project at the University of Pennsylvania (UPenn) (NIH R03HD069742), two placenta measures were collected during gestation and one at delivery (n=600). The dataset also contains gestational weight gain and fetal biometric parameters. The University of Connecticut (UConn) study was conducted in over 400 women who gave birth between 22-32 weeks of gestation. Study data contained adverse pregnancy outcomes, maternal and neonate demographics, and placental morphology measures. The Pennington Biomedical Research Center (PBRC) placental data can be collected as an ancillary to the existing U01. Ultrasound recordings of the placenta can be collected during the first, second, third trimesters and digital photographs at term are being collected in 80 overweight and obese women. Weekly body weights, body composition, total energy expenditures by the doubly labeled water method, resting metabolic rate, energy intake assessed by two different objective methods (model and energy balance), and appetite hormones can also collected.

The adverse pregnancy risk model will be constructed from data obtained from the sub population with placental measures at more than one time point; WUSL (n=81), NYU (n=80), UPenn (n=300), PBRC (n=80). Cases with placental measures collected at only one time point will be used to determine ranges of normal versus at risk placental measure at those specific time points.

A key time point in growth is the inflection point, when the curve switches from exponential growth behavior to a log-like behavior. The invention disclosed herein uses the logistic growth model and, for example, two placental volume databases, one with 5 longitudinal measures of placental volume determined by three-dimensional ultrasound and the second with 2 measures (one early and one at term) to first, calculate the timing of the inflection point in healthy pregnancies, second, whether deviations of inflection timing predict pregnancy complications and finally, generating predictions utilizing solely early pregnancy data. In a further embodiment, the invention couples the dynamic placental volume model with a placental-fetal scaling law to arrive at a dynamic fetal growth model that generates fetal growth curves after input of placental growth parameters.

Assumptions, Definitions and Mathematical Embodiments of the Invention

| Assumption | Assumption Statement |
|---|---|
| 1 | The early rate of placental volume growth is directly proportional to placental volume. |
| 2 | Initial growth is limited by a saturation value beyond which the placental volume cannot increase. |
| 3 | The self-limiting component of the model is described by multiplying the term which exhibits exponential growth by a limiting factor, $\left(1 - \frac{P}{K}\right)$. |
| 4 | Both the proportionality constant, r, and the carrying capacity, K, are independent of time. |

| Variable and Parameter Definitions | | |
|---|---|---|
| Variable/Parameter | Definition | Units |
| P(t) | The placental volume on day t of gestation | mL |
| r | The placental volume growth rate in early gestation is directly proportional to the current placental volume. The value of r is the proportionality constant. | 1/d |
| K | The carrying capacity of the placenta which is the absolute possible limiting volume the placenta cannot exceed. | mL |
| $P_0$ | The volume of the placenta in the first trimester (~84 days). | mL |
| Time of Inflection Point | The time point when as the placental volume curve shifts from concave up to concave down in the S shape. | Gestational day |
| α | α = (Placental Weight)$^{3/4}$ | g/g$^{3/4}$ |
| β | ¾ | |

Placental volume (mL) increases over gestation and thus is a time-varying quantity. In order to express this dependency of placental volume on time, placental volume (mL) was denoted on gestational day t by $P_V(t)$. The derivative of $P_V(t)$, denoted $$\frac{dP_V}{dt},$$

represents the growth rate of placental volume and is expressed in units mL/d where d represents days.

The inventive placental volume model is a differential equation that relates the derivative of placental volume to a function of placental volume, $f(P_V)$ (formulation of $f(P_V)$ is described in the next section):

$$\frac{dP_V}{dt} = f(P_V)$$

The solution of the differential equation yields a value that represents the expected or predicted placental volume on any given gestational day, t. Described below is the derivation of the function $f(P_V)$, and the solution of the placental volume model.

The Placental Volume Model

Every differential equation model entails a number of assumptions. These assumptions serve two purposes. The first is to sufficiently simplify the model so that it can be solved mathematically. The second reflects what is known about the specific mechanics of the model. For example, placental volume is known to increase sigmoidally over gestation. Therefore the model assumes this growth pattern. The list that follows outlines some assumptions underlying the placental volume model formulation:

(A1) The early growth rate of placental volume is directly proportional to placental volume, rP, where r is the proportionality constant. Conceptually, this assumption is made because early placental growth is due to cell division which is well known to follow this growth pattern.

(A2) The increase in placental volume over gestation is eventually limited by a maximum value beyond which placental volume cannot increase. This saturation value is referred to as the "placental carrying capacity" in mL and denoted by the value, K. The carrying capacity is not the placental volume at term, but rather the upper bound beyond which placental volume cannot increase.

(A3) This self-limiting property of placental growth is captured by multiplying the early growth term, $rP_V$, by a limiting factor $$\left(1 - \frac{P_V}{K}\right)$$

which has the property that, when P is close to K, the factor is close to zero.

(A4) Both the proportionality constant, r, and the carrying capacity, K, are time-independent. Formulating these assumptions, Applicants arrived at the placental volume growth model:

$$\frac{dP_V}{dt} = rP_V\left(1 - \frac{P_V}{K}\right).$$

The initial values and parameters must be non-negative: $P_V(t_0) \geq 0$ and r, $K \geq 0$, where $t_0$ represents the gestational day at first placental volume measurement. In one embodiment, the first measured placental volume was obtained at approximately 12 weeks (84 days) so $t_0 = 84$ days and the initial condition is (84), the mL of placental volume at 84 days.

The Placental Volume Model Solution

The model, $$\frac{dP_V}{dt} = rP_V\left(1 - \frac{P_V}{K}\right),$$

can be solved explicitly for the solution P(t).

$$P_V(t) = \frac{KP_0 e^{-84r}}{e^{-rt}K - e^{-rt}P_0 + P_0 e^{-84r}}$$

where $P_0$ represents the initial measurement of placental volume (here measured at approximately 84 days of gestation). This explicit solution has three parameters, r, K and $P_0$ (bolded in the formula), which are calculated from the data. Once these values are entered, the solution yields an expected placental volume for gestational day, otherwise stated, a prediction for P(t).

Determination of Model Parameters and Timing of Inflection

To fit three parameters in a model, here the values of r, K and $P_0$, a minimum of three placental volume measurements across gestation are needed. The multi-point database contains five placental volume measurements in each of the 11 pregnancies, and so three measurements from the five to fit the parameters can be used Parameter Fitting Method Using the Multi-Point Study Data Below is provided an example of model solution from an individual placenta. In the given example, placental volume at week 12 (84 days) was 54.8 mL, at week 17 (119 days) placental volume was 130.9 mL and at week 32 (224 days), 380.9 mL.

Step 1: Set the Initial Value, $P_0$, Equal to the Measured Volume at 12 Weeks.

In this example, $P_0 = 54.8$. Fitting in this value into the solution yields:

$$P_V(t) = \frac{7102Ke^{-84r}}{125e^{-rt}K + 7102e^{-84r} - 7102e^{-rt}}$$

Step 2: Use the 32-Week Measured Placental Volume to Solve for K in Terms of r.

Substituting t=224 days, provides for:

$$P_V(224) = \frac{7102Ke^{-84r}}{125e^{-r224}K + 7102e^{-84r} - 7102e^{-r224}}$$

or for this example:

$$380.9 = \frac{7102Ke^{-84r}}{125e^{-r224}K + 7102e^{-84r} - 7102e^{-r224}}$$

This is an algebraic equation which can be solved for K:

$$K = \frac{208733.2(e^{-84r} - e^{-224r})}{548e^{-84r} - 3809e^{-224r}}$$

Substituting this expression of K back into the formula for P(t) yields:

$$P_V(t) = \frac{208733.2(e^{-84r} - e^{-224r})}{3261e^{-r(t+84)} + 584e^{-168r} - 3809e^{-308r}}$$

Step 3: Apply the 17-Week (119 Day) Placental Volume Measurement to Solve for r.

Substituting t=119 days, provides for:

$$P_V(119) = \frac{208733.2(e^{-84r} - e^{-224r})}{3261e^{-r(119+84)} + 584e^{-168r} - 3809e^{-308r}}$$

$$130.9 = \frac{208733.2(e^{-84r} - e^{-224r})}{3261e^{-r(203)} + 584e^{-168r} - 3809e^{-308r}}$$

which can be solved for r:

r=0.032.

Step 4: Substitute the Value of r into the Formula for K to Solve for K.

$$K = \frac{208733.2(e^{-84r} - e^{-224r})}{548e^{-84r} - 3809e^{-224r}} = 409.8 \text{ mL}$$

So, the predictive formula for placental volume becomes:

$$P_V(t) = \frac{1156.8}{355.0e^{-0.32t} + 3.8}$$

Figure 2:
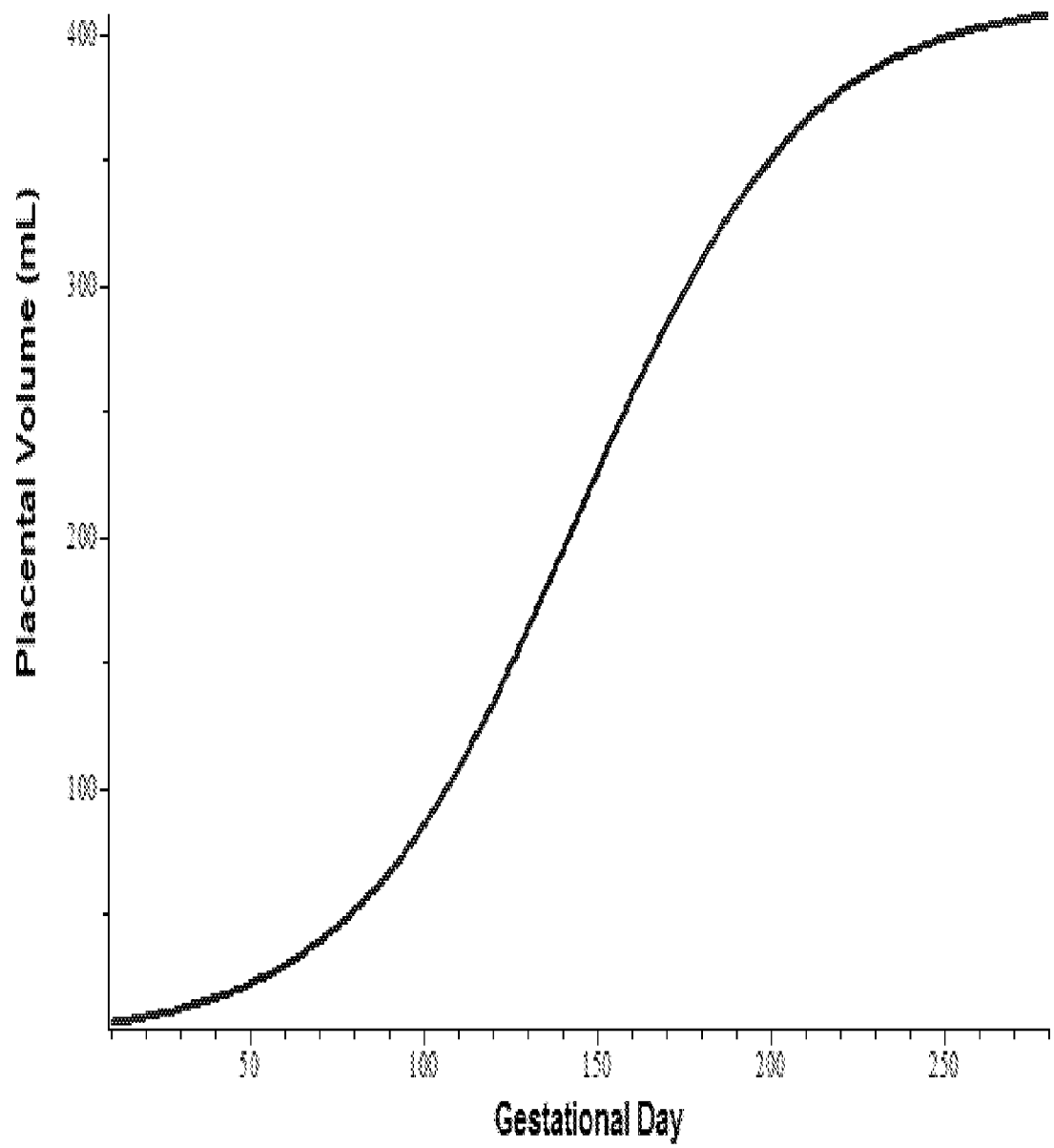
FIG. 2 shows the sigmoidal curve when gestational day is plotted against placental volume.

Graphing this function from t=0 to 280 (40 weeks) yields the S shaped (sigmoidal) (FIG. 2).

Step 5: Calculate the Gestational Day of Inflection by Setting $$P_V(t) = \frac{K}{2}$$

From the model, the timing of inflection of the sigmoidal curve can be calculated. At the point of inflection, the placental volume is half the carrying capacity. Substituting $$P_V(t) = \frac{K}{2}$$

yields an algebraic formula:

$$\frac{1156.8}{355.0e^{-0.32t} + 3.8} = 204.9$$

Solving for t yields the timing of inflection: t=1418 days or 20.4 weeks.

Parameter Fitting Method Using the Early Pregnancy Study Data

Unfortunately, obtaining placental volume measurements is time-consuming and it is rare to have more than one measured volume during gestation, especially when the number of study participants is larger than N=10. Since only one measured gestational placental volume is in the early pregnancy database, and a delivery measure of placental weight, additional assumptions are needed to estimate the three parameters.

The first point was a measured placental volume obtained approximately at 12-weeks (84 days) of gestation. The second point was a placental weight at term. Although placental density is not well established and may have high inter-individual variance, a density of 1 was applied for conversion, which is consistent with that of adipose tissue (0.9 g/mL[5]) and muscle (1.06 g/mL[6]).

Recall that two placental volume measurements are insufficient to fit all three parameters, r, K, and P_0. The timing of inflection in the multi-point study was clustered between 19-21 weeks of gestation. Therefore, it was assumed that the timing of inflection in the early pregnancy study should also occur at ~20 weeks gestation.

Similar to the step by step description of parameter estimates in the multi-point study, data from a subject was applied to illustrate the calculations. For this example placental volume at 84 days was $P_V(84)=117.9$ mL, gestational age at term was 259 days, and placental volume at term was 355.0 mL.

Step 1: Set the Initial Value, $P_0$, Equal to the Measured Volume at 12 Weeks.

In the case of this example, $P_0=117.9$. Filling in this value into the solution yields:

$$P_V(t) = \frac{117.9Ke^{-84r}}{e^{-rt}K - 117.9e^{-rt} + 117.9e^{-84r}}$$

Step 2: Solve for K in Terms of r by Setting t=Gestational Age at Term and $P_V$=Placental Volume at Term.

For this example t=259 and P=355 mL:

$$355 = \frac{117.9Ke^{-84r}}{e^{-r259}K - 117.9e^{-r259} + 117.9e^{-84r}}$$

which yields:

$$K = \frac{418545(e^{-84r} - e^{-259r})}{1179e^{-84r} - 3550e^{-259r}}$$

Substituting K into the solution:

$$P_V(t) = \frac{41854.5e^{-84r}(e^{-84r} - e^{-259r})}{237.1e^{-r(t+84)} + 117.9e^{-168r} - 355e^{-342r}}$$

Step 3: Solve for r by Assuming the Gestational Age at Inflection is 20 Weeks (140 Days) and Solving $$P_V(140) = \frac{K}{2} \text{ for } r.$$

t=140 days is set as equal to $$\frac{K}{2},$$

the value of P at the point of inflection.

$$\underbrace{\frac{41854.5e^{-84r}(e^{-84r} - e^{-259r})}{237.1e^{-r(140+84)} + 117.9e^{-168r} - 355e^{-342r}}}_{P_V(140)} = \left(\frac{1}{2}\right)\underbrace{\left(\frac{418545(e^{-84r} - e^{-259r})}{1179e^{-84r} - 3550e^{-259r}}\right)}_{K}$$

This equation contains only one unknown parameter, r. Solving for r yields, r=0.02

Now that all constants are known, the final formula for P(t) is expressed by:

$$P_V(t) = \frac{24955.7}{579.3e^{-0.02t} + 61.2}$$

Derivation of Dynamic Fetal Weight Model

In another embodiment, the invention applies the validated fetal-placental scaling law which states that placental weight is proportional to fetal weight to a fractional power $P_W = \alpha(t)FW^\beta$ where $P_W$ represents the grams of placental weight and FW represents grams of fetal weight. The value of the scaling exponent, β, has been determined as ¾ while the time-varying proportionality constant α(t) is known to be 1 at term[8].

Step 1 Let ρ Represent the Density of the Placenta (Assume ρ=1 for Numerical Calculations) and Substitute $P_W = \rho P_V$ into the Fetal-Placental Scaling Law:

$$P_W = \alpha(t)FW^\beta \Rightarrow \rho P_V = \alpha(t)FW^\beta \Rightarrow P_V = \frac{\alpha(t)}{\rho}FW^\beta$$

Step 2 Calculate the Derivative of $P_V$ in Terms of FW:

$$\frac{dP_V}{dt} = \frac{\alpha(t)}{\rho}\beta FW^{\beta-1}\frac{dFW}{dt} + \frac{\alpha'(t)}{\rho}FW^\beta$$

Step 3: Substitute the Scaling Law Expression, $$P_V = \frac{\alpha(t)}{\rho}FW^\beta.$$

into the Placental Volume Differential Equation:

$$\frac{dP_V}{dt} = rP_V\left(1 - \frac{P_V}{K}\right) = r\frac{\alpha(t)}{\rho}FW^\beta\left(1 - \frac{\alpha(t)FW^\beta}{\rho K}\right)$$

Step 4: Equate the Expression in Step 2 with the Expression in Step 3 and Solve for $$\frac{FW}{dt}: \frac{\alpha(t)}{\rho}\beta FW^{\beta-1}\frac{dFW}{dt} + \frac{\alpha'(t)}{\rho}FW^\beta = r\frac{\alpha(t)}{\rho}FW^\beta\left(1 - \frac{\alpha(t)FW^\beta}{\rho K}\right)$$

$$\Rightarrow \frac{\alpha(t)}{\rho}\beta FW^{\beta-1}\frac{dFW}{dt}$$

$$= r\frac{\alpha(t)}{\rho}FW^\beta\left(1 - \frac{\alpha(t)FW^\beta}{\rho K}\right) -$$

$$\frac{\alpha'(t)}{\rho}FW^\beta$$

$$\Rightarrow \frac{\beta}{\rho}\frac{dFW}{dt}$$

$$= \frac{r}{\beta}FW\left(1 - \frac{\alpha(t)FW^\beta}{\rho K}\right) - \frac{\alpha'(t)}{\alpha(t)\rho}FW$$

$$\Rightarrow \frac{dFW}{dt}$$

$$= \frac{r}{\beta}FW\left(1 - \frac{\alpha(t)FW^\beta}{\rho K}\right) - \frac{\alpha'(t)}{\alpha(t)\beta}FW$$

After input of the parameters, r β, ρ, K, and α(t), the solution to this model generates a predicted fetal growth curve, FW(t).

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Subjects

The first database included longitudinal measures of placental volume at weeks 12, 17, 22, 27, and 32 weeks of pregnancy in twelve healthy women. This database is referred to as the multi-point study. From these data, the parameters of the logistic growth model were calculated, and then solved for the gestational age at inflection. The second database was comprised of 54 women that included measures of a placental volume at 11-14 weeks of pregnancy and the delivered placental weight. Since the only in utero measurement of the placenta was early in pregnancy, this study is referred to as the early pregnancy study. This database contained 11 complicated pregnancies. With these 11 "abnormal outcomes", tests were performed to determine whether deviations from the inventive placental volume growth model predicted at risk pregnancies. Both studies were approved by their institutional review boards.

Example 1

The Multi-Point Study

Pregnant women who answered posted advertisements were recruited from two private practice obstetrical offices in Northern New Jersey. Subjects were eligible for the study if they were between 18 and 35 years old and were less than 12 weeks pregnant at enrollment confirmed by first trimester ultrasonography. Women were excluded for: 1. History of smoking and/or drug abuse, 2. A history of gestational diabetes or preeclampsia in a prior pregnancy, 3. Medical co-morbidities (i.e. chronic hypertension, diabetes, asthma, etc), and 4. Known uterine anomalies or fibroids. Data from enrolled participants were excluded from the analysis if gestational diabetes or preeclampsia was diagnosed during the study period. 20 women responded and 13 were qualified to participate in the study. Of these, one was diagnosed with gestational diabetes during the study pregnancy. Physical and other characteristics of the 12 women who completed the study are shown in FIG. 10.

Subjects underwent measurements of maternal height and weight at weeks 12, 17, 22, 27, and 32 weeks of gestation. For placental volume measurement, the entire view of the placenta was identified by 2-D ultrasonography, and the volume box was adjusted to scan the entire placenta. The sweep angle was set at 85° and was aimed so that the probe was perpendicular to the placental plate. Placental volume scans were then obtained by 3D ultrasonography. All volume scans were stored on a removable hard drive for volume calculation at a later date. Three scans were obtained at each time point, and the average of the three volumes scans was used for each time point. All images were acquired using Voluson E8 Ultrasound machines (GE Medical Systems, Milwaukee, Wis., USA) with a 4- to 8-MHz transducer. All ultrasounds were performed by one of two perinatologists.

In order to estimate placental volume, evaluation of the entire placenta was performed using the rotational technique in the virtual organ computer-aided analysis (VOCAL) program included in the 4DVIEW 6.0 software (GE, Austria) computer software. Measurements were performed on the sagittal section ("A" plane used as the reference image) by manually contouring the surface of the placenta, rotating the image 6 degrees and contouring the surface again. This process was repeated 30 times until completing an 180° rotation. After completion of the rotation, the VOCAL software yielded placental volume estimation as well as a computed 3D reconstruction of the placental. Care was taken to exclude the uterine wall during manual contouring. Manual contours were performed by the one physician.
Calculation of Missing 32-Week Placental Volume Only six out of the 11 women in the multi-point study had a 32-week placental volume measure. By comparing the six data points at 32 weeks with 27 week data, it was found that 32 week placental volume was highly correlated to 27 week volume ($R^2$=0.79). Missing data was imputed using the regression formula: $P_{32}$=0.92$P_{27}$+166.6, where $P_{27}$, $P_{32}$ represent 27-week and 32-week volumes, respectively.

Example 2

The Early Pregnancy Study

A more detailed description of the original study appears in Schwartz N, Coletta J, Pessel C, Feng R, Timor-Tritsch I E, Parry S, et al. Novel 3-dimensional placental measurements in early pregnancy as predictors of adverse pregnancy outcomes. J Ultrasound Med. 2010; 29(8):1203-12, which is incorporated by reference in its entirety. The original study recruited pregnant women between 11 to 14 weeks' gestation from the Philadelphia metropolitan region. The study was designed to determine whether early measurements of placental morphology predicted pregnancy outcomes. From the 98 subjects in the original study, 54 had both measurements of placental volume at 11-14 weeks and placental weight at (term) delivery, who were the subsample in this analysis. A transabdominal probe (Voluson E8; GE Healthcare, Milwaukee, Wis.) was used to obtain a 3D volume sweep of the placenta. The volumes were obtained using power Doppler imaging (quality, maximum; pulse repetition frequency, 0.6 kHz; and gain adjusted to just below the snow artifact) with the sweep angle opened to ensure inclusion of the entire placenta. The volume was reacquired if an obvious fetal motion artifact occurred during the sweep or if it appeared that a substantial portion of the placenta was excluded from the sweep. Volumes were stored for offline analysis postpartum.

The placental volume sets were then manipulated using 4D View software (GE Healthcare, Kretztechnik, Zipf, Austria). The placental volume was isolated using virtual computer-aided analysis, which involves manual tracing the perimeter of the placenta in successive images as obtained by automatic rotation of the image 6 times around the y-axis in 30° intervals to achieve a 180° rotation. With these traced perimeters, the software reconstructs the shape and volume of the object.

Demographic data, such as maternal age, parity, race, and body mass index (BMI), as well as pregnancy outcome data, including gestational age at delivery, birth weight, and pregnancy complications, were collected from the hospital medical records. Gestational age at delivery was based on first trimester sonographic dating if a definite last menstrual period was not available or if there was a greater than 7-day discrepancy between menstrual dating and first-trimester sonographic biometric measurements. Preeclampsia was defined as the finding of a systolic blood pressure of 140 mm Hg or higher or a diastolic blood pressure of 90 mm Hg or higher on 2 occasions 6 hours apart in the presence of substantial proteinuria, defined as a 24-hour urine collection containing greater than 300 mg of protein or urine dipstick with a 1+ protein value or higher. Birth weight percentiles were determined on the basis of the curve of Alexander et al., with small for gestational age (SGA) defined by birth weight at or below the $10^{th}$ percentile for the completed gestational week.

Example 3

The Logistic Model for Placental Volume

The logistic model solutions are sigmoidal curves. Sigmoidal growth curves are experimentally observed in placental growth, which has made the logistic model a natural choice for placental growth models (8, 16). Specifically, the logistic model is a differential equation originating from population ecology (17). If $P_V(t)$ is defined as the mL of placental volume on day t of gestation then the model is given by the differential equation:

$$\frac{dP_V}{dt} = rP_V\left(1 - \frac{P_V}{K}\right)$$

where r is exponential growth rate during early placental growth and K is the carrying capacity. The carrying capacity, K, represents the upper bound for placental volume past which the placental volume cannot increase. In order to simulate the model, an initial value of placental volume, $P_0$, (preferably measured during early pregnancy) is required. A complete mathematical and biological background of the logistic growth model was provided above.

Example 4

Parameter Calculations in the Multi-Point Study

All parameter calculations were performed in Maple 12 (Waterloo, Canada 2012) interfaced with Microsoft Excel 2011 (Seattle, Wash. 2011). Three parameters that need to be determined; $P_0$, r, and the carrying capacity, K. Using the 12-week (84 day) measured placental volume for $P_0$, this value was substituted into the solution of the logistic model:

$$P_V(t) = \frac{KP_0 e^{-84r}}{e^{-rt}(K - P_0) + P_0 e^{-84r}}$$

The 32-week (224 days) placental volume measurement was used to calculate K, setting $P_V(224)=P_{32}$ and solving for K:

$$K = \frac{P_0 P_{32}(e^{-84r} - e^{-224r})}{P_0 e^{-84r} - P_{32} e^{-224r}}$$

Next, the 17-week (119 days) placental volume measurement was used to solve for r. Specifically, r is calculated by solving the algebraic equation:

$$\frac{KP_0 e^{-84r}}{e^{-r(119)}(K - P_0) + P_0 e^{-84r}} = P_{17}$$

where $P_{17}$ is the 17-week measured placental volume.

Calculation of the Gestational Age at Inflection Point

The inflection point occurs when the second derivative is zero, which is calculated directly from the differential equation:

$$\frac{d^2 P}{dt^2} = r\frac{dP}{dt} - \frac{2rP}{K}\frac{dP}{dt} = \frac{dP}{dt}\left(1 - \frac{2P}{K}\right) = 0$$

$$\Rightarrow P = \frac{K}{2}$$

After input of $P_0$, r, and, solving for t in the algebraic equation:

$$\frac{KP_0 e^{-84r}}{e^{-rt}(K - P_0) + P_0 e^{-84r}} = \frac{K}{2}$$

yields the time (as gestational age in days) of inflection.

Example 5

Placental Volume Model Validation

Placental volume data from weeks 22 and weeks 27 in the multi-point study was not applied to determine parameters and therefore can be used to determine model accuracy. A Bland Altman analysis was performed in Microsoft Excel 2011 (Seattle, Wash. 2011) to test model agreement with the placental volume at weeks 22 and weeks 27.

Example 6

Parameter Calculations in the Early Pregnancy Study

From the analysis of the multi-point study, the timing of the inflection point in healthy pregnancies was determined to be between 19-21 weeks of gestation. The gestational age was set at inflection point at 20 weeks (140 days) and assumed a first placental volume measurement at 12 weeks (84 days). Similar to the analysis in multi-point study, 84 days was set as initial time and $P_0$ equal to the initial placental volume measurement. The experiment computed r by substituting t=140 and solving the equation:

$$\frac{KP_0 e^{-84r}}{e^{-r140}(K - P_0) + P_0 e^{-84r}} = \frac{K}{2}$$

for the non-zero solution of r. Finally, the experiment used the at term placental weight data to solve for K, by setting t=GA (gestational age at delivery) and solving the algebraic equation:

$$\frac{KP_0 e^{-84r}}{e^{-rGA}(K - P_0) + P_0 e^{-84r}} = P_{final}$$

where $P_{final}$ represents the final volume at term (converted from placental weight using a density of approximately 1). Expanded details with a numerical example were provided above.

Example 7

Estimating Pregnancy Risk as Deviations from Model Predictions

While analysis of parameters using at term measurements is informative, it is not desirable for risk detection during pregnancy. By applying average parameter estimates from the multi-point study where all pregnancies were normal, the experiment examined whether deviations from model predictions from the early pregnancy study was related to pregnancy complications. In order to rely solely on early pregnancy data to estimate model parameters, the experiment used the exponential model:

$$P_V(t) = P_0 e^{r(t-84)}$$

with r set as the average value from the multi-point data set (r=0.03) and $P_0$ set as the first trimester ultrasound measured placental volume in the early pregnancy study. As calculated earlier in the methods, the value of placental volume at the inflection point is $$\frac{K}{2}.$$

Assuming the inflection point must occur at 20 weeks (119 days), then solving the equation:

$$K = 2(P_0 e^{r(119-84)})$$

results in a rough estimate for K. Now that $P_0$, r, and K are known, a predictive placental volume curve can be simulated and compared to actual placental volume at term. The deviation of the actual placental volume at term from the model predictions was calculated to determine whether the actual volume "fell off the curve". The number of pregnancy complications were grouped by quartiles of distance that the actual placental volume deviated from the predicted curve.

Example 8

Prediction of Pregnancy Complications in the Early Pregnancy Study

If parameter estimates were derived from both 12-week placental volume and at term placental weight, the values of r and K were grouped by quartiles and the number of pregnancy complications summed by quartile. When only the 11-14 week data was used to fit parameters, the values of r, and the difference between actual and predicted placental volume at term (error) were grouped into quartiles and the number of pregnancy complications were summed accordingly.

Example 9

Fetal Growth Model

The experiment applied the validated fetal-placental scaling law which states that placental weight is proportional to fetal weight to a fractional power $P_W = \alpha(t) FW^\beta$ where $P_W$ represents the grams of placental weight and FW represents grams of fetal weight. The value of the scaling exponent, $\beta$, has been well-established as ¾ while the time-varying proportionality constant $\alpha(t)$ is known to be 1 at term.

By substituting the fetal-placental relationship into the placental volume differential equation model (expanded calculations shown above), a differential equation model was derived in terms of fetal growth that rely on the placental growth parameters, r and K:

$$\frac{dFW}{dt} = \frac{r}{\beta} FW \left(1 - \frac{\alpha(t) FW^\beta}{K}\right) - \frac{\alpha'(t)}{\alpha(t)\beta} FW$$

where FW(t) represents fetal weight on the $t^{th}$ gestational day.

Once r, $\beta$, $\alpha(t)$, and K were inputted, the model was simulated to generate a fetal growth curve. For numerical simulations an explicit formula for $\alpha(t)$ and fetal weight at 12 weeks is required. For this purpose, a best fit curve ($R^2 = 0.97$) for data was applied:

$$\alpha(t) = 247.97 t^{-0.974}$$

Twelve week fetal weight was estimated as 20 g and all numerical simulations were performed in Maple 12 (Waterloo, CANADA 2012).

Example 10

Validation and Analysis of Fetal Growth Model

The multi-point study contained all required information (r, K, gestational age at term, and birthweights) to compare actual versus predicted birth weights. A Bland Altman analysis was performed in Microsoft Excel (Seattle, Wash. 2011) to validate the fetal growth model.

Fetal growth curves were generated for different combinations of r and in the estimated data determined parameter ranges. The ranges of r (0.02-0.04) and K (378-840 mL) were separated into low r (r=0.02), average r (r=0.03), high r (r=0.04) and low K (K=378 mL), average K (K=582 mL) and high K (K 850 mL) and fetal growth curves were simulated to term (gestational age of 40 weeks). The resulting predicted birth weight was classified into small for gestational age (SGA), average for gestational age (AVA) or large for gestational age (LGA) in the ranges <2500 g, between 2500 and 4000 g, and above 4000 g respectively.

Example 11

Results

Parameter Estimates

FIG. 11 contains the breakdown of parameter estimates (X±SD) by study, pregnancies without complications, pregnancies with complications, and total pregnancies. In the early pregnancy study, the mean value of r was lower in the pregnancies with complications than in the uncomplicated pregnancies. When r was grouped by quartiles, eight out of the eleven (73%) pregnancies with complications were in the two lower quartiles of r. Similar associations were not found for the carrying capacity, K, and first trimester placental volume, $P_0$.

Estimation of Gestational Age at Inflection Point

The gestational age at inflection ranged from 19.4-28.8 weeks with a median at 20.8 weeks and a mean of 22.2±3.4 weeks (FIG. 11).

Placental Volume Model Validation

The correlation between actual placental volume and predicted placental volume at 22 weeks was $R^2=0.75$ which reduced to $R^2=0.62$ at 27 weeks (FIG. 3 Panels A and B). There was an overestimation of placental volume at both 22 and 27 weeks with a bias of −37.5 mL at 22 weeks (95% confidence interval of [−92.4, 17.1]) and a bias of −59.0 mL at 27 weeks (95% confidence interval of [−158.0, 40.1]).

Parameter Estimates, Model Predictions and Pregnancy Risks Relying Solely on Early Pregnancy Data (Exponential Model)

Figure 5:
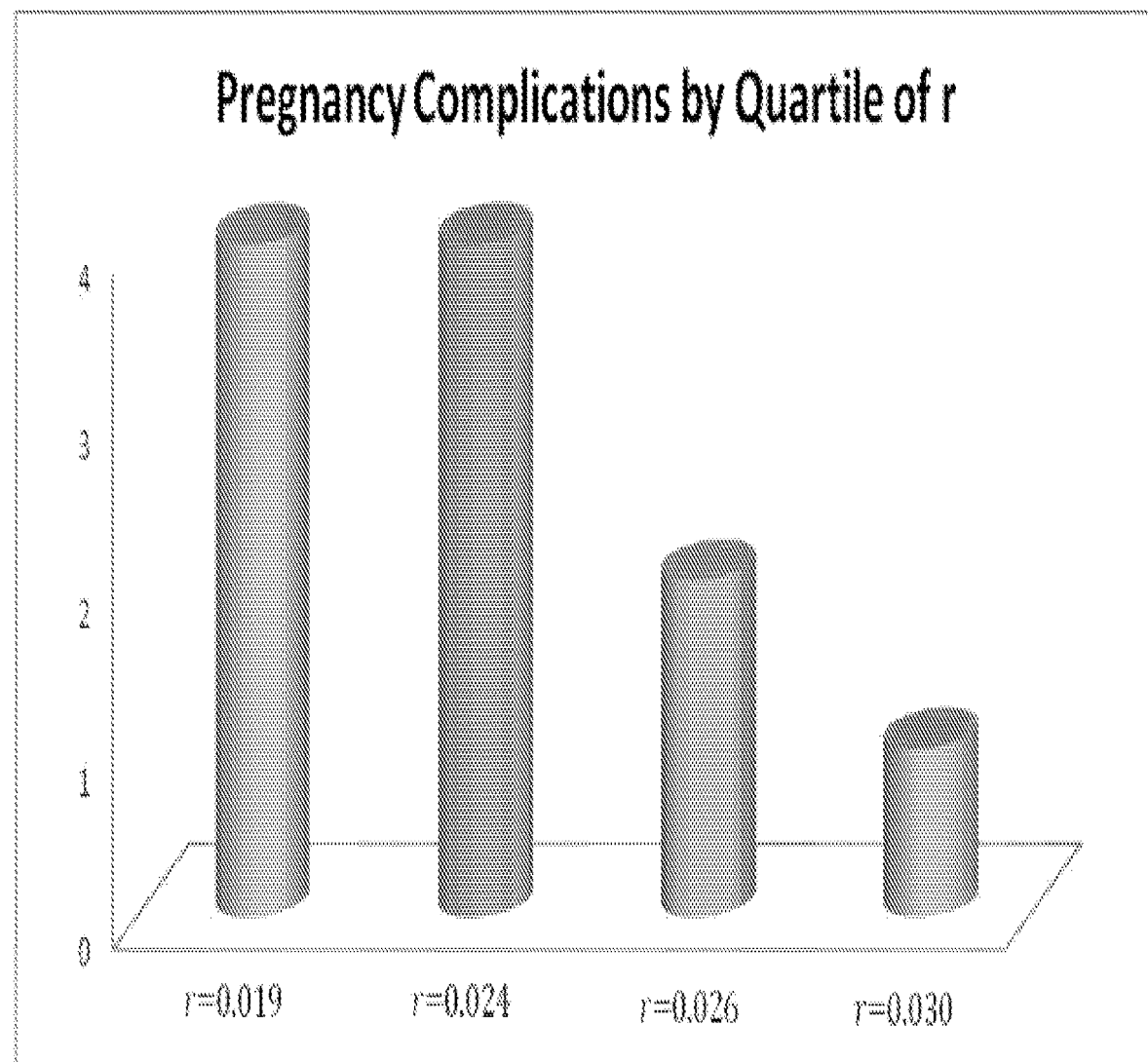
FIG. 5 shows the number of pregnancy complications by quartile of the parameter r.

The values for K were higher than estimated with the logistic model. This is expected since the exponential model will overestimate placental volume because it lacks any growth limiting parameter. Thus, the difference between actual final volume and predicted final volume will trend downward and negative. Arrangement of the error by quartiles as shown in FIG. 5 revealed that seven of the eleven (64%) of the pregnancies with complications were located in the two bottom quartiles of error. The two bottom quartiles of error represented the highest deviations between actual and predicted.

Fetal Growth Model Validation

The correlation between actual birth weight and predicted birth weight was $R^2=0.36$ which (FIG. 3, Panel C). The model overestimated birth weight (bias=−675.1 g, confidence interval: [−2157.8, 807.7]).

Fetal Growth Model Analysis

Only 3 combinations of r and K resulted in a birth weight AGA; low r and average K, average r and low K, low r and average K, and low r and high K (FIG. 9). The value of r influenced early fetal growth while the value of K impacted later fetal growth (FIG. 4). While the theoretical simulations of all combinations of r and K were possible, the experimental data revealed that low r was most often paired with high K, average r was paired with a K value around 400 mL, and high r was paired with low K. In both studies, there were no cases of low r values paired with low K values. The model correctly classified 7 of the 11 (64%) of the birth weights with the four misclassifications resulting in a predicted LGA versus an actual AGA at term.

Thus, as shown in the Examples above, the invention rigorously calculated the gestational age at point of inflection for the growth of placenta at approximately 20 weeks. The point of inflection has also been referred to as the maximal growth rate of the placenta. The inventors applied this point of inflection and the logistic growth model to classify risks in a dataset of 54 pregnancies. It was discovered that that lower values of the initial growth rate, was associated with pregnancy complications. Also discovered was an association with deviations from placental volume model predictions and pregnancy complications.

The combination of the inventively developed dynamic placental volume model and a well-established fetal-placental scaling law resulted in a dynamic fetal growth model which exhibited the influence of placental parameters on fetal growth. This analysis advances the field which has predominately relied on statistical relationships between placental measures and birth outcomes by permitting users to input placental parameters and observe the fetal growth curve at any gestational time point. The fetal growth model informs how placental growth affects fetal development at various stages during pregnancy. Interestingly, the fetal model indicated how different birth weights can be arrived at using various combinations of placental growth parameters. Additionally, the lack of any data with low values of r and K indicated that some parameter combinations are not physiologically feasible.

REFERENCES

1. Salafia C M, Misra D P, Yampolsky M, Charles A K, Miller R K. Allometric metabolic scaling and fetal and placental weight. Placenta. 2009; 30(4):355-60. Epub 2009/03/07. doi: S0143-4004(09)00017-4 [pii] 10.1016/j.placenta.2009.01.006. PubMed PMID: 19264357.
2. Salafia C M, Yampolsky M, Misra D P, Shlakhter O, Haas D, Eucker B, et al. Placental surface shape, function, and effects of maternal and fetal vascular pathology. Placenta. 2010; 31(11):958-62. Epub 2010/10/12. doi: 50143-4004 (10)00339-5 [pii] 10.1016/j.placenta.2010.09.005. PubMed PMID: 20933281; PubMed Central PMCID: PMC2964412.
3. Yampolsky M, Salafia C M, Shlakhter O, Haas D, Eucker B, Thorp J. Centrality of the umbilical cord insertion in a human placenta influences the placental efficiency. Placenta. 2009; 30(12):1058-64. Epub 2009/11/03. doi: 10.1016/j.placenta.2009.10.001. PubMed PMID: 19879649; PubMed Central PMCID: PMC2790011.
4. Yampolsky M, Salafia C M, Shlakhter O, Haas D, Eucker B, Thorp J. Modeling the variability of shapes of a human placenta. Placenta. 2008; 29(9):790-7. Epub 2008/08/05. doi: S0143-4004(08)00186-0 [pii] 10.1016/j.placenta.2008.06.005. PubMed PMID: 18674815; PubMed Central PMCID: PMC2570048.
5. Yampolsky M, Salafiaa C M, Shlakhtera O, Misraa5 D P, Haasa D, Euckera B, et al. Variable placental thickness affects placental functional efficiency independent of other placental shape abnormalities. Journal of Developmental Origins of Health and Disease 2011; 2(4):205-2011.
6. Schwartz N, Mandel D, Shlakhter O, Coletta J, Pessel C, Timor-Tritsch I E, et al. Placental morphologic features and chorionic surface vasculature at term are highly correlated with 3-dimensional sonographic measurements at 11 to 14 weeks. J Ultrasound Med. 2011; 30(9):1171-8. Epub 2011/08/31. doi: 30/9/1171 [pii]. PubMed PMID: 21876086.
7. Hafner E, Philipp T, Schuchter K, Dillinger-Paller B, Philipp K, Bauer P. Second-trimester measurements of placental volume by three-dimensional ultrasound to predict small-for-gestational-age infants. Ultrasound Obstet Gynecol. 1998; 12(2):97-102. Epub 1998/09/23. doi: 10.1046/j.1469-0705.1998.12020097.x. PubMed PMID: 9744052.
8. Rizzo G, Capponi A, Cavicchioni O, Vendola M, Arduini D. First trimester uterine Doppler and three-dimensional ultrasound placental volume calculation in predicting pre-eclampsia. Eur J Obstet Gynecol Reprod Biol. 2008; 138(2):147-51. Epub 2007/10/06. doi: S0301-2115(07) 00364-8 [pii] 10.1016/j.ejogrb.2007.08.015. PubMed PMID: 17916401.
9. Hafner E, Metzenbauer M, Hofinger D, Munkel M, Gassner R, Schuchter K, et al. Placental growth from the first to the second trimester of pregnancy in SGA-foetuses and pre-eclamptic pregnancies compared to normal foetuses. Placenta. 2003; 24(4):336-42. Epub 2003/03/27. PubMed PMID: 12657506.
10. Schwartz N, Coletta J, Pessel C, Feng R, Timor-Tritsch I E, Parry S, et al. Novel 3-dimensional placental measurements in early pregnancy as predictors of adverse pregnancy outcomes. J Ultrasound Med. 2010; 29(8): 1203-12. Epub 2010/07/28. doi: 29/8/1203 [pii]. PubMed PMID: 20660454.
11. Odibo A O, Zhong Y, Longtine M, Tuuli M, Odibo L, Cahill A G, et al. First-trimester serum analytes, biophysical tests and the association with pathological morphometry in the placenta of pregnancies with preeclampsia and fetal growth restriction. Placenta. 2011; 32(4):333-8. Epub 2011/02/18. doi: S0143-4004(11)00027-0 [pii] 10.1016/j.placenta.2011.01.016. PubMed PMID: 21324404.
12. Kim Y M, Chaiworapongsa T, Gomez R, Bujold E, Yoon B H, Rotmensch S, et al. Failure of physiologic transformation of the spiral arteries in the placental bed in preterm premature rupture of membranes. Am J Obstet Gynecol. 2002; 187(5):1137-42. Epub 2002/11/20. PubMed PMID: 12439491.
13. Kim Y M, Bujold E, Chaiworapongsa T, Gomez R, Yoon B H, Thaler H T, et al. Failure of physiologic transformation of the spiral arteries in patients with preterm labor and intact membranes. Am J Obstet Gynecol. 2003; 189(4):1063-9. Epub 2003/10/31. PubMed PMID: 14586356.
14. McMaster-Fay R A. Failure of physiologic transformation of the spiral arteries of the uteroplacental circulation in patients with preterm labor and intact membranes. Am J Obstet Gynecol. 2004; 191(5):1837-8; author reply 8-9. Epub 2004/11/18. doi: 10.1016/j.ajog.2004.05.091. PubMed PMID: 15547578.
15. Odibo A O, Goetzinger K R, Huster K M, Christiansen J K, Odibo L, Tuuli M G. Placental volume and vascular flow assessed by 3D power Doppler and adverse pregnancy outcomes. Placenta. 2011; 32(3):230-4. Epub 2011/ 02/08. doi: S0143-4004(11)00021-X [pii] 10.1016/j.placenta.2011.01.010. PubMed PMID: 21295850; PubMed Central PMCID: PMC3125967.
16. Barker D J, Bull A R, Osmond C, Simmonds S J. Fetal and placental size and risk of hypertension in adult life. BMJ. 1990; 301(6746):259-62. Epub 1990/08/04. PubMed PMID: 2390618; PubMed Central PMCID: PMC1663477.
17. Barker D J, Thornburg K L, Osmond C, Kajantie E, Eriksson J G. The surface area of the placenta and hypertension in the offspring in later life. The International journal of developmental biology. 2010; 54(2-3): 525-30. Epub 2009/10/31. doi: 10.1387/ijdb.082760db. PubMed PMID: 19876839.
18. Risnes K R, Romundstad P R, Nilsen T I, Eskild A, Vatten L J. Placental weight relative to birth weight and long-term cardiovascular mortality: findings from a cohort of 31,307 men and women. Am J Epidemiol. 2009;

170(5):622-31. Epub 2009/07/30. doi: 10.1093/aje/kwp182. PubMed PMID: 19638481.
19. Moore V M, Miller A G, Boulton T J, Cockington R A, Craig I H, Magarey A M, et al. Placental weight, birth measurements, and blood pressure at age 8 years. Arch Dis Child. 1996; 74(6):538-41. Epub 1996/06/01. PubMed PMID: 8758133; PubMed Central PMCID: PMC1511556.
20. Higgins M F, Russell N M, Mooney E E, McAuliffe F M. Clinical and ultrasound features of placental maturation in pre-gestational diabetic pregnancy. Early Hum Dev. 2012; 88(10):817-21. Epub 2012/07/04. doi: 10.1016/j.earlhumdev.2012.06.001. PubMed PMID: 22749772.
21. Salafia C M, Yampolsky M. Metabolic scaling law for fetus and placenta. Placenta. 2009; 30(5):468-71. Epub 2009/03/17. doi: S0143-4004(08)00438-4 [pii] 10.1016/j.placenta.2008.12.013. PubMed PMID: 19285342; PubMed Central PMCID: PMC2699210.
22. Salafia C M, Ghidini A, Minior V K. Uterine allergy: a cause of preterm birth? Obstet Gynecol. 1996; 88(3):451-4. Epub 1996/09/01. doi: 0029-7844(96)00219-0 [pii] 10.1016/0029-7844(96)00219-0. PubMed PMID: 8752257.
23. Egbor M, Ansari T, Morris N, Green C J, Sibbons P D. Pre-eclampsia and fetal growth restriction: how morphometrically different is the placenta? Placenta. 2006; 27(6-7):727-34. Epub 2005/08/30. doi: S0143-4004(05)00180-3 [pii] 10.1016/j.placenta.2005.06.002. PubMed PMID: 16125226.
24. Schuchter K, Metzenbauer M, Hafner E, Philipp K. Uterine artery Doppler and placental volume in the first trimester in the prediction of pregnancy complications. Ultrasound Obstet Gynecol. 2001; 18(6):590-2. Epub 2002/02/15. doi: 596 [pii] 10.1046/j.0960-7692.2001.00596.x. PubMed PMID: 11844195.
25. Hafner E, Metzenbauer M, Hofinger D, Stonek F, Schuchter K, Waldhor T, et al. Comparison between three-dimensional placental volume at 12 weeks and uterine artery impedance/notching at 22 weeks in screening for pregnancy-induced hypertension, pre-eclampsia and fetal growth restriction in a low-risk population. Ultrasound Obstet Gynecol. 2006; 27(6):652-7. Epub 2006/03/04. doi: 10.1002/uog.2641. PubMed PMID: 16514618.
26. Semczuk-Sikora A, Krzyzanowski A, Stachowicz N, Robak J, Kraczkowski J, Kwiatek M, et al. [Maternal serum concentration of angiogenic factors: PlGF, VEGF and VEGFR-1 and placental volume in pregnancies complicated by intrauterine growth restriction]. Ginekol Pol. 2007; 78(10):783-6. Epub 2008/01/19. PubMed PMID: 18200969.
27. Higgins M, Felle P, Mooney E E, Bannigan J, McAuliffe F M. Stereology of the placenta in type 1 and type 2 diabetes. Placenta. 2011; 32(8):564-9. Epub 2011/05/31. doi: S0143-4004(11)00169-X [pii] 10.1016/j.placenta.2011.04.015. PubMed PMID: 21621839.
28. Gauster M, Desoye G, Totsch M, Hiden U. The placenta and gestational diabetes mellitus. Curr Diab Rep. 2012; 12(1):16-23. Epub 2011/11/22. doi: 10.1007/s11892-011-0244-5. PubMed PMID: 22102097.
29. Akhter F, Ferdausi R. Quantitative macroscopic study on preterm placenta in gestational diabetes mellitus and pregnancy induced hypertension. Mymensingh Med J. 2011; 20(2):280-6. Epub 2011/04/28. PubMed PMID: 21522101.
30. McNamara J M, Odibo A O. Sonographic evaluation and the pregnancy complicated by diabetes. Curr Diab Rep. 2011; 11(1):13-9. Epub 2010/11/04. doi: 10.1007/s11892-010-0158-7. PubMed PMID: 21046292.
31. Treacy A, Higgins M, Kearney J M, McAuliffe F, Mooney E E. Delayed villous maturation of the placenta: quantitative assessment in different cohorts. Pediatr Dev Pathol. 2013; 16(2):63-6. Epub 2012/11/10. doi: 10.2350/12-06-1218-OA.1. PubMed PMID: 23137099.
32. Salafia C M, Yampolsky M, Shlakhter A, Mandel D H, Schwartz N. Variety in placental shape: when does it originate? Placenta. 2012; 33(3):164-70. Epub 2012/01/06. doi: S0143-4004(11)00574-1 [pii] 10.1016/j.placenta.2011.12.002. PubMed PMID: 22217910.
33. Yampolsky M, Salafia C M, Shlakhter O. Probability distributions of placental morphological measurements and origins of variability of placental shapes. Placenta. 2013; 34(6):493-6. Epub 2013/04/09. doi: 10.1016/j.placenta.2013.03.003. PubMed PMID: 23562224.
34. Gill J S, Salafia C M, Grebenkov D, Vvedensky D D. Modeling oxygen transport in human placental terminal villi. J Theor Biol. 2011; 291:33-41. Epub 2011/10/01. doi: S0022-5193(11)00464-4 [pii] 10.1016/j.jtbi.2011.09.008. PubMed PMID: 21959313.
35. Costa A, Costantino M L, Fumero R. Oxygen exchange mechanisms in the human placenta: mathematical modelling and simulation. J Biomed Eng. 1992; 14(5):385-9. Epub 1992/09/01. PubMed PMID: 1405555.
36. Groome L J. A theoretical analysis of the effect of placental metabolism on fetal oxygenation under conditions of limited oxygen availability. Biosystems. 1991; 26(1):45-56. Epub 1991/01/01. PubMed PMID: 1760534.
37. Thomas D M, Clapp J F, Shernce S. A foetal energy balance equation based on maternal exercise and diet. J R Soc Interface. 2008; 5(21):449-55 PMID: 1789522. Epub 2007/09/27. doi: J8JK099G66V7546L [pii] 10.1098/rsif.2007.1161. PubMed PMID: 17895222; PubMed Central PMCID: PMC2607387.
38. de Paula C F, Ruano R, Campos J A, Zugaib M. Placental volumes measured by 3-dimensional ultrasonography in normal pregnancies from 12 to 40 weeks' gestation. J Ultrasound Med. 2008; 27(11):1583-90. Epub 2008/10/24. doi: 27/11/1583 [pii]. PubMed PMID: 18946097.
39. Redmer D A, Milne J S, Aitken R P, Johnson M L, Borowicz P P, Reynolds L P, et al. Decreasing maternal nutrient intake during the final third of pregnancy in previously overnourished adolescent sheep: effects on maternal nutrient partitioning and feto-placental development. Placenta. 2012; 33(2):114-21. Epub 2011/12/14. doi: S0143-4004(11)00555-8 [pii] 10.1016/j.placenta.2011.11.023. PubMed PMID: 22154692.
40. Thomas L, Wallace J M, Aitken R P, Mercer J G, Trayhurn P, Hoggard N. Circulating leptin during ovine pregnancy in relation to maternal nutrition, body composition and pregnancy outcome. J Endocrinol. 2001; 169(3):465-76. Epub 2001/05/26. doi: JOE04159 [pii]. PubMed PMID: 11375117.
41. van Abeelen A F, de Rooij S R, Osmond C, Painter R C, Veenendaal M V, Bossuyt P M, et al. The sex-specific effects of famine on the association between placental size and later hypertension. Placenta. 2011; 32(9):694-8. Epub 2011/07/12. doi: S0143-4004(11)00233-5 [pii] 10.1016/j.placenta.2011.06.012. PubMed PMID: 21742377.
42. Hasegawa J, Nakamura M, Hamada S, Okuyama A, Matsuoka R, Ichizuka K, et al. Gestational weight loss has adverse effects on placental development. J Matern Fetal Neonatal Med. 2012. Epub 2012/02/22. doi: 10.3109/14767058.2012.664666. PubMed PMID: 22348351.

43. Schoeller D A, Thomas D, Archer E, Heymsfield S B, Blair S N, Goran M I, et al. Self-report-based estimates of energy intake offer an inadequate basis for scientific conclusions. Am J Clin Nutr. 2013; 97(6):1413-5. Epub 2013/05/22. doi: 10.3945/ajcn.113.062125. PubMed PMID: 23689494.

44. Lichtman S W, Pisarska K, Berman E R, Pestone M, Dowling H, Offenbacher E, et al. Discrepancy between self-reported and actual caloric intake and exercise in obese subjects. N Engl J Med. 1992; 327(27):1893-8. Epub 1992/12/31. doi: 10.1056/NEJM199212313272701. PubMed PMID: 1454084.

45. Schoeller D A. How accurate is self-reported dietary energy intake? Nutr Rev. 1990; 48(10):373-9. Epub 1990/10/01. PubMed PMID: 2082216.

46. Butte N F, Wong W W, Treuth M S, Ellis K J, O'Brian Smith E. Energy requirements during pregnancy based on total energy expenditure and energy deposition. Am J Clin Nutr. 2004; 79(6):1078-87. Epub 2004/05/26. PubMed PMID: 15159239.

47. Goldberg G R, Prentice A M, Coward W A, Davies H L, Murgatroyd P R, Wensing C, et al. Longitudinal assessment of energy expenditure in pregnancy by the doubly labeled water method. Am J Clin Nutr. 1993; 57(4):494-505. Epub 1993/04/01. PubMed PMID: 8460604.

48. Thomas D M, Navarro-Barrientos J E, Rivera D E, Heymsfield S B, Bredlau C, Redman L M, et al. Dynamic energy-balance model predicting gestational weight gain. Am J Clin Nutr. 2012; 95(1):115-22 PMCID: 3238455. Epub 2011/12/16. doi: ajcn.111.024307 [pii] 10.3945/ajcn.111.024307. PubMed PMID: 22170365; PubMed Central PMCID: PMC3238455.

49. Thomas D M, Halawani M, Phelan S, Butte N F, Redman L M. Development of a pregravid weight calculator: Insights into the validity of self-reported pregravid weight in overweight and obese pregnant women. Under Review at Obstetrics & Gynecology. 2013.

50. Thomas D M, Urena B. A model describing the evolution of West Nile-like encephalitis in New York City. Mathematical and Computer Modelling. 2001; 34(7-8):771-81.

51. Dudley N J. A systematic review of the ultrasound estimation of fetal weight. Ultrasound Obstet Gynecol. 2005; 25(1):80-9. Epub 2004/10/27. doi: 10.1002/uog.1751. PubMed PMID: 15505877.

It is to be understood that the invention is not limited to the particular embodiments of the invention described above, as variations of the particular embodiments may be made and still fall within the scope of the appended claims.

We claim:

1. A method for predicting a prenatal, neonatal, obstetric or childhood clinical event, disease or disorder from data collected during a pregnancy, comprising the steps of:
    inputting periodically collected pregnancy data comprising placental and obstetric data into a database housed in a computer;
    applying a continuous recursion modeling algorithm to said inputted pregnancy data to generate fetal and placental growth data during said pregnancy;
    generating data showing any deviations from model predictions of normal fetal and placental growth when compared to said generated fetal and placental growth data during said pregnancy; and
    predicting a prenatal, neonatal, obstetric or childhood risk of an adverse clinical event, disease or disorder from said deviating data.

2. The method according to claim 1, further comprising the step of performing a clinical intervention if said deviating data so warrants.

3. The method according to claim 1, wherein said continuous recursion modeling algorithm is housed in a computer.

4. The method according to claim 1, wherein said prenatal, neonatal, obstetric or childhood clinical event, disease or disorder is preeclampsia, intrauterine growth restriction, preterm labor, stillbirth, type 2 diabetes, high diastolic blood pressure, high systolic blood pressure,
    increased presence of placental knots, fibrotic chorionic villi, intrauterine growth restrict, intraventicular hemorrhage, placental edema, fetal acute inflammation, chorioamnionitis, amnion necrosis, acute fetal inflammation, acute maternal inflammation or acute amnionitis.

5. The method of claim 1, wherein the periodically collected pregnancy data is data periodically collected during pregnancy of a given subject.

6. The method of claim 5, wherein the periodically collected pregnancy data is placental measures collected at multiple times during gestation.

7. The method of claim 1, wherein the periodically collected pregnancy data is from 3D ultrasound images of the placenta.

8. The method of claim 1, wherein the periodically collected pregnancy data is obtained early in the pregnancy.

9. The method of claim 8, wherein the periodically collected pregnancy data is obtained within 11-14 weeks of gestation.

10. The method of claim 8, wherein the periodically collected pregnancy data is from 3D ultrasound images of the placenta obtained within 11-14 weeks of gestation.

11. The method of claim 1, wherein the method allows for observing the fetal growth curve at any gestational time point.

12. The method of claim 1, wherein the method informs how placental growth affects fetal development at various stages during pregnancy.

13. A method for generating in-utero fetal and placental growth curves from data collected during a pregnancy, comprising the steps of:
    inputting placental and obstetric data collected from said pregnancy into a database housed in a computer; and
    applying a continuous recursion modeling algorithm to said pregnancy data to generate said in-utero fetal and placental growth curves during said pregnancy.

14. A computer programmed to predict a prenatal, neonatal, obstetric or childhood clinical event, disease or disorder from data collected during a pregnancy, comprising software which:
    applies a continuous recursion modeling algorithm to data collected during said pregnancy, and inputted into said computer, to generate in-utero fetal and placental growth data; and
    outputs data showing any deviations of said in-utero fetal and placental growth data from model predictions of normal in-utero fetal and placental growth.

15. The computer according to claim 14, wherein said software further predicts a prenatal, neonatal, obstetric or childhood risk of an adverse clinical event, disease or disorder from said outputted data showing deviations.

16. An article of manufacture for predicting a prenatal, neonatal, obstetric or childhood clinical event, disease or disorder from data periodically collected during a pregnancy, comprising:

a non-transitory computer-readable storage medium, and code stored on the medium, the code, when executed on a processor, controlling the processor for measuring in-utero fetal and placental growth during said pregnancy, wherein the processor applies a continuous recursion modeling algorithm to said data periodically collected during said pregnancy to show any deviations of said data periodically collected during said pregnancy from model values of normal placental volume to predict said prenatal, neonatal, obstetric or childhood clinical event, disease or disorder.

* * * * *